(12) United States Patent
Swearingen et al.

(10) Patent No.: US 12,295,610 B2
(45) Date of Patent: *May 13, 2025

(54) ULTRASONIC SURGICAL INSTRUMENT

(71) Applicant: REACH SURGICAL, INC., Tianjin (CN)

(72) Inventors: Lily Swearingen, Clarksville, OH (US); Jean Beaupre, Alexandria, KY (US)

(73) Assignee: Reach Surgical, Inc., Tianjin (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/133,396

(22) Filed: Apr. 11, 2023

(65) Prior Publication Data

US 2024/0050119 A1    Feb. 15, 2024

Related U.S. Application Data

(63) Continuation of application No. 16/623,214, filed as application No. PCT/US2018/037728 on Jun. 15, 2018, now Pat. No. 11,622,788.

(60) Provisional application No. 62/520,491, filed on Jun. 15, 2017.

(51) Int. Cl.
    *A61B 17/32*      (2006.01)
    *A61B 17/00*      (2006.01)

(52) U.S. Cl.
    CPC ............... *A61B 17/320092* (2013.01); *A61B 2017/0046* (2013.01); *A61B 2017/00477* (2013.01); *A61B 2017/320094* (2017.08)

(58) Field of Classification Search
CPC .. A61B 17/320092; A61B 2017/00477; A61B 2017/320094; A61B 2017/0046; A61B 2017/292; A61B 2017/2929
See application file for complete search history.

(56) References Cited

U.S. PATENT DOCUMENTS

| | | | |
|---|---|---|---|
| 2008/0021278 A1* | 1/2008 | Leonard | A61B 17/1608 600/129 |
| 2015/0182250 A1* | 7/2015 | Conlon | A61B 17/320092 606/169 |
| 2016/0151071 A1* | 6/2016 | Tokarz | A61B 17/1285 606/143 |

* cited by examiner

*Primary Examiner* — Ashley L Fishback
(74) *Attorney, Agent, or Firm* — Porter Wright Morris & Arthur LLP

(57) ABSTRACT

Ultrasonic surgical instrument having a handle assembly, a waveguide extending distally from handle assembly, an end-effector at distal end of the waveguide, and a clamp assembly removably mounted to the handle assembly. The clamp assembly includes a pivotally mounted clamp arm for pivotal movement with respect to the end effector, and is removably mounted to the handle assembly by axially aligned first and second bayonet mounts. Each of the bayonet mounts includes a female bayonet coupling having at least one bayonet slot configured to matingly receive a bayonet mounting pin of a male bayonet coupling, wherein the bayonet slots extend circumferentially about the longitudinal axis of the waveguide. A method of removing the clamp assembly of the ultrasonic surgical instrument is also provided, as well as an ultrasonic surgical shears instrument and a clamp assembly.

20 Claims, 15 Drawing Sheets

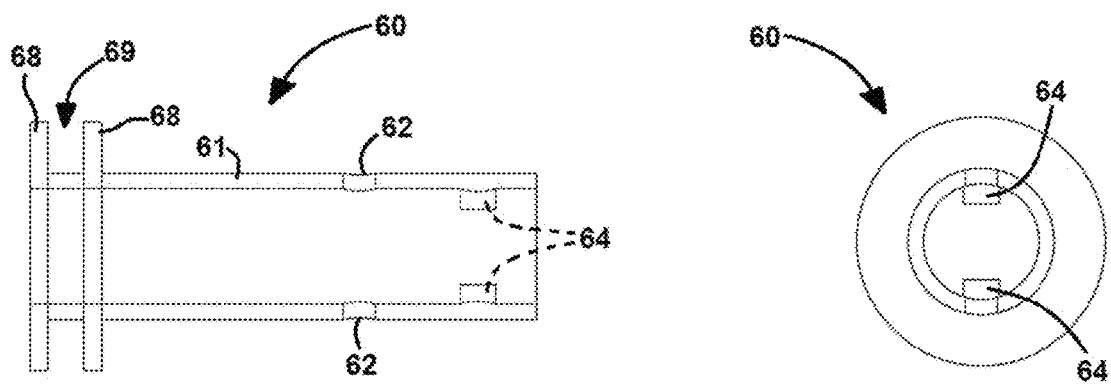
FIG. 9A
FIG. 9B
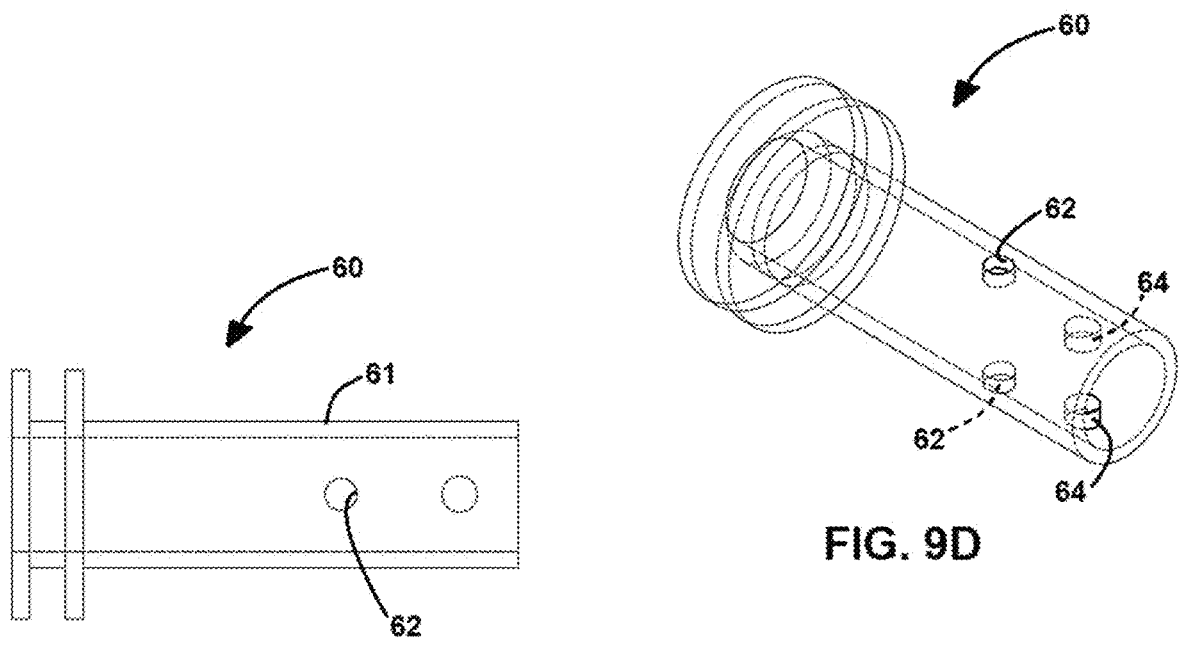
FIG. 9C
FIG. 9D

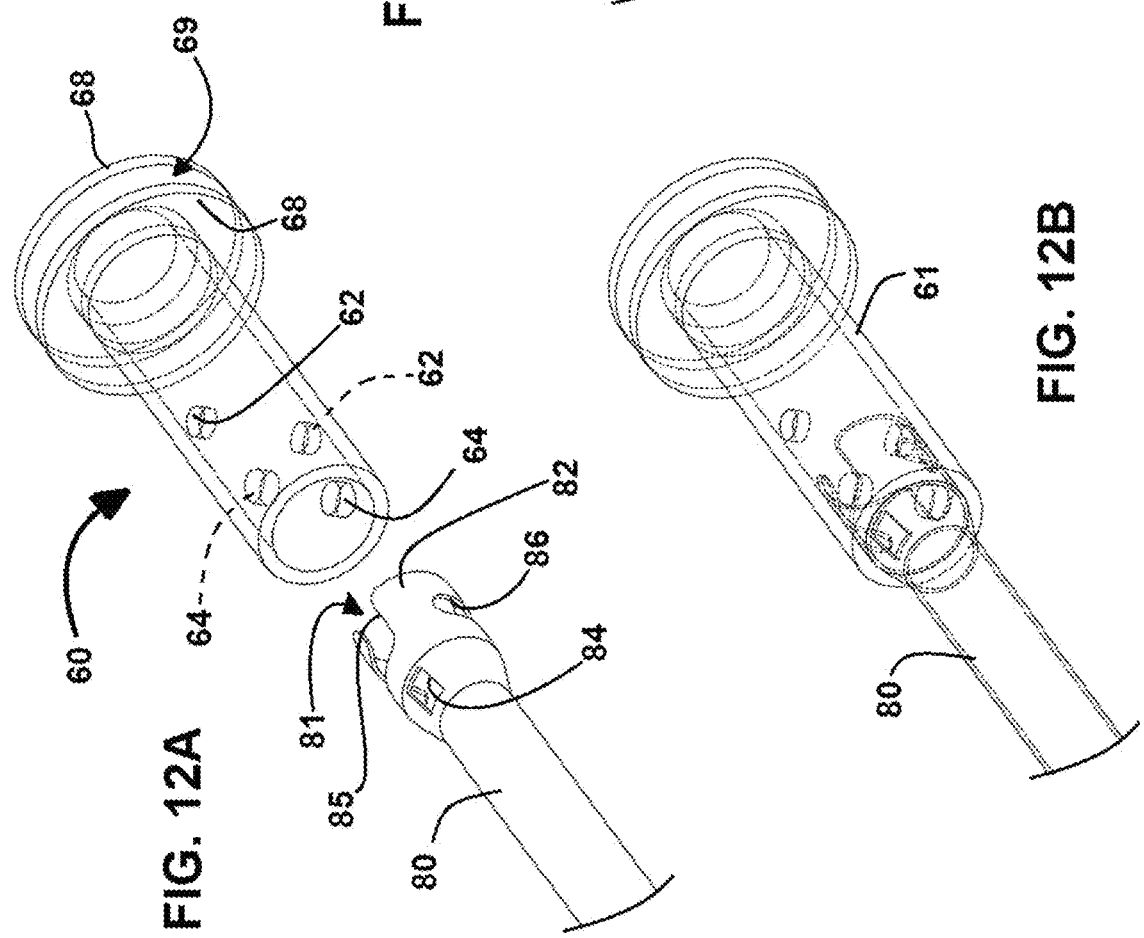

ULTRASONIC SURGICAL INSTRUMENT

CROSS REFERENCE TO RELATED APPLICATIONS

This application is a continuation of U.S. patent application Ser. No. 16/623,214, filed Dec. 16, 2019, which issued on Apr. 11, 2023 as U.S. Pat. No. 11,622,788, and was a national stage entry under section 371 of International App. No. PCT/US2018/037728, filed Jun. 15, 2018, which claimed priority to U.S. Provisional Patent Application No. 62/520,491, filed on Jun. 15, 2017, entitled "ULTRASONIC SURGICAL INSTRUMENT," filed on Jun. 15, 2017. This application is related to U.S. Provisional Patent Application No. 62/264,672, filed on Dec. 8, 2015, entitled "ULTRASONIC SURGICAL INSTRUMENT," and International App. No. PCT/US2016/065543, filed on Dec. 8, 2016, entitled "ULTRASONIC SURGICAL INSTRUMENT." The entire disclosures of the foregoing patent applications are incorporated by reference herein.

BACKGROUND

Ultrasonic surgical instruments have been used for quite some time in the cutting, coagulation and/or dissection of tissue during various medical procedures. Compared to conventional static scalpels, for example, ultrasonically driven blades typically require less force for cutting tissue, and can also provide coagulation of blood vessels—particularly when the instrument includes a clamp arm associated with the blade. Energy in the form of mechanical vibrations at ultrasonic frequencies is transmitted to a surgical end-effector. Ultrasonic surgical instruments are particularly advantageous because of the amount of ultrasonic energy that may be transmitted from an ultrasonic transducer to the surgical end-effector via a waveguide. Such instruments are particularly suited for use in minimally invasive surgery, such as endoscopic or laparoscopic procedures, wherein the end-effector is typically passed through a trocar or other small opening to reach the surgical site.

Ultrasonic surgical end-effectors, also referred to as blades, are usually provided at the end of an elongate waveguide, which in turn is operatively coupled to an ultrasonic transducer. The transducer, often provided as part of, or housed within, a handpiece, is adapted to convert electrical energy (typically supplied by an external generator) into vibrational motion, typically longitudinal vibrations, at an ultrasonic frequency. In many instances, the transducer includes a "Langevin stack" of piezoelectric disks for this purpose. The standing wave produced by the transducer is transmitted from the transducer to the waveguide, and propagates the length of the waveguide to the blade located at the distal end of the waveguide. As a result, the blade vibrates at an ultrasonic frequency.

When the ultrasonically vibrating blade is urged against tissue, such as by manipulation of a handpiece and/or by clamping tissue between the vibrating blade and a clamp arm, the mechanical vibratory energy of the blade is transmitted to the tissue, not only cutting the tissue but also generating frictional heat and causing cavitation, coaptation and coagulation of the tissue. Such devices having a blade and associated clamp arm for urging tissue against the ultrasonically vibrating blade are referred to as ultrasonic shears (also known as clamp coagulators or ultrasonic forceps). Tissue is urged against the ultrasonic blade (or end-effector) by a movable clamp arm that opposes at least a portion of the blade. During use, tissue positioned between the clamp arm and the blade is compressed against the blade as the clamp arm is closed. As a result, the clamped tissue is cut and coagulated.

A variety of ultrasonic clamp coagulators (or ultrasonic shears) adapted for use in surgery and, more particularly, for use in minimally invasive surgery, are well known in the art. For example, U.S. Pat. Nos. 6,214,023 and 5,322,055, each of which is incorporated by reference herein, illustrate ultrasonic clamp coagulators that utilize clamp arms to apply pressure to tissue, forcing contact between tissue and an end-effector provided at the distal end of an ultrasonic waveguide. The clamp arm typically includes a pad, often made from a polymer such as PTFE (e.g., Teflon) in order to prevent direct contact between the end-effector and the clamp arm (both of which are typically metal). The clamp pad, however, can become worn or contaminated during use, often requiring the entire instrument to be discarded.

The clamp coagulator instruments described in U.S. Pat. No. 6,214,023 include a replaceable pad and clamp arm. However, while the clamp pad and clamp arm on these instruments can be replaced, removal of the pad/clamp arm leaves the elongated waveguide and its surrounding outer sheath in place, making the instrument difficult to clean and re-sterilize.

Thus, it would be advantageous to provide a simple and cost effective way to replace worn or contaminated clamp arms while also making the instrument easy to clean and re-sterilize. It would also be advantageous to provide a means for attaching sterile clamp arms during surgical procedures. It would also be advantageous to provide ultrasonic surgical shears particularly adapted to allow simple removal and replacement of clamp arms for cleaning and sterilization.

While a variety of devices and techniques may exist for providing ultrasonic surgical instruments such as ultrasonic shears having replaceable components, it is believed that no one prior to the inventor has made or used an invention as described herein.

BRIEF DESCRIPTION OF THE DRAWINGS

While the specification concludes with claims particularly pointing out and distinctly claiming the invention, it is believed that the invention will be better understood from the detailed description of certain embodiments thereof when read in conjunction with the accompanying drawings. Unless the context indicates otherwise, like numerals are used in the drawings to identify similar elements in the drawings. In addition, some of the figures may have been simplified by the omission of certain elements in order to more clearly show other elements. Such omissions are not necessarily indicative of the presence or absence of particular elements in any of the exemplary embodiments, except as may be explicitly stated in the corresponding detailed description.

FIGS. 9A-D are top, side, perspective and front views, respectively, of the second coupling member of the male bayonet connector assembly.

FIGS. 12A-C schematically illustrate the mounting of the inner tubular actuation member to the second coupling member, with the outer support tube and the first coupling member omitted for clarity.

Figure 1:
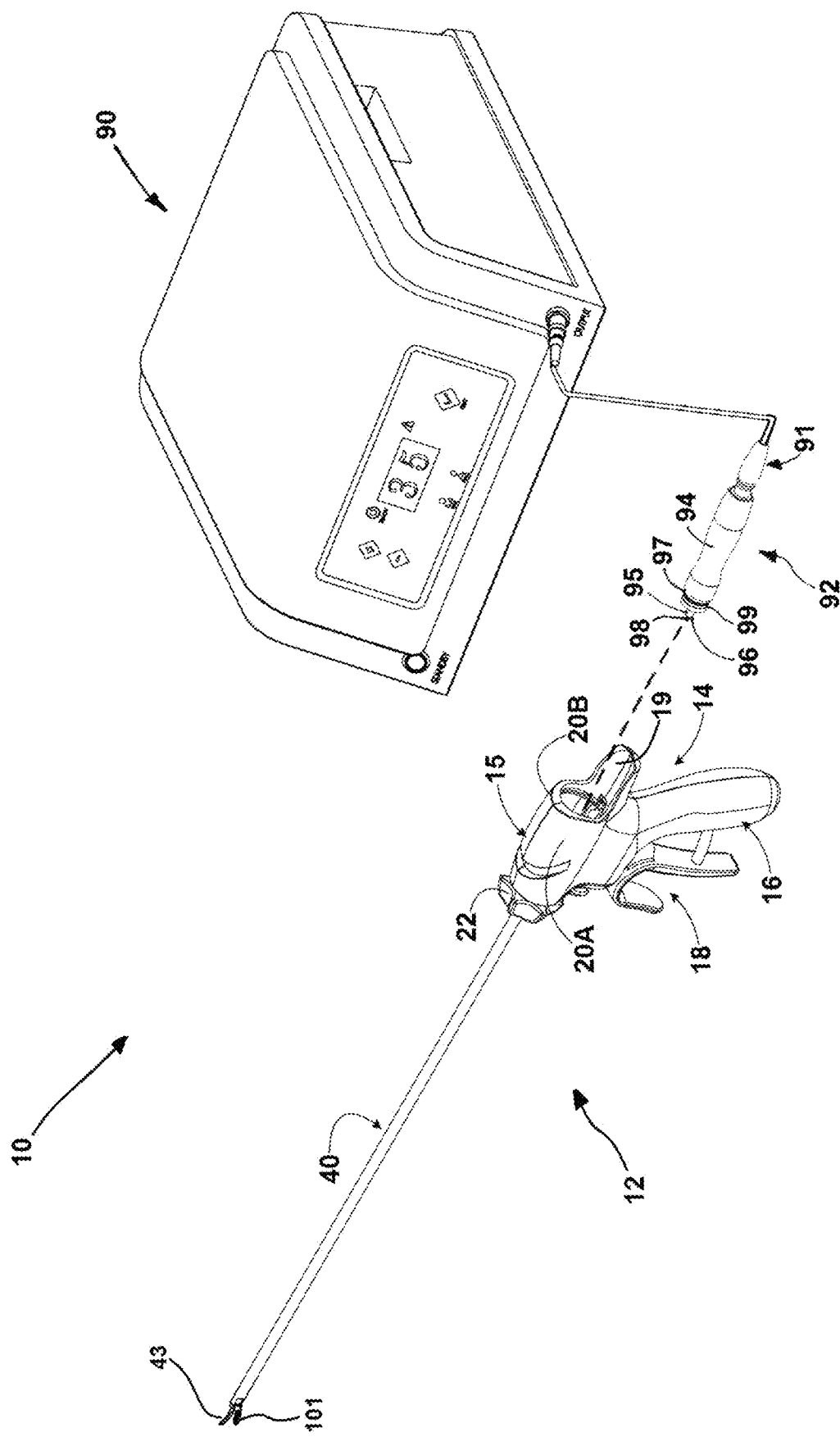
FIG. 1 is a perspective view of one embodiment of an ultrasonic surgical system.

The drawings are intended to illustrate rather than limit the scope of the present invention. Embodiments of the present invention may be carried out in ways not necessarily depicted in the drawings. Thus, the drawings are intended to merely aid in the explanation of the invention. Thus, the present invention is not limited to the precise arrangements shown in the drawings.

DETAILED DESCRIPTION

The following detailed description describes examples of embodiments of the invention solely for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention.

The present disclosure relates generally to medical devices comprising an elongate outer tubular member and an inner elongate shaft (solid or tubular) located at least partially within the outer tubular member, wherein the tubular member and shaft are mountable to a handle assembly (or other housing) at a proximal end of the tubular member/shaft using a pair of axially aligned bayonet mounts. Each of the bayonet mounts comprises a female bayonet coupling and a mating, male bayonet coupling. In some embodiments, the male bayonet couplings (each in the form of one or more mounting pins) are provided on the handle assembly, while the female bayonet couplings are provided on a proximal end portion of each of the tubular member and shaft. Each of the female bayonet couplings comprises at least one bayonet slot configured to matingly receive a mounting pin of the corresponding male bayonet coupling therein, wherein a portion of each of the bayonet slots extends circumferentially (straight or helical) about a common longitudinal axis (i.e., coaxial bayonet mounts). In some embodiments, the male bayonet couplings are arranged such that the second male bayonet coupling is provided on a second coupling member that is at least partially received within the interior of a first coupling member on which the first male bayonet coupling is provided, with the coupling members arranged to allow for axial, sliding movement of at least a portion of the second coupling member with respect to the first coupling member. The coupling members, in some embodiments, are also configured to prevent relative rotation between the first and second coupling members as well as to limit the amount of axial sliding movement permitted. In still further embodiments the second coupling member is at least partially retained within the first coupling member by a coupling pin that extends through a pair of apertures (or elongate slots) on opposite sides of the first coupling member, a pair or apertures (or elongate slots) on opposite sides of the second coupling member, and through the waveguide. By providing the elongate slots instead of apertures on at least one of the coupling members, axial sliding movement of one coupling member with respect to the other is permitted with the extent of such reciprocal movement defined by the length of the elongate slots.

In some embodiments, the dual bayonet mounting arrangement can also be used to transmit both rotational and axial forces to the outer tubular member and inner shaft (or tube) assembly. For example, a bayonet connector assembly comprising the first and second coupling members can be used to mount the outer tubular member/inner shaft (or tube) assembly to a handle assembly, wherein the handle assembly is configured to selectively (e.g., using an actuating lever) impart reciprocal, axial movement of one coupling member with respect to the other coupling member. The reciprocated coupling member will thus cause the outer tubular member to be reciprocated over the inner shaft/tube, or cause the inner shaft/tube to be reciprocated within the outer tubular member—depending on which of the outer tubular member and inner shaft/tube is mounted to the reciprocated coupling member. Rotational movement can also be transmitted to the outer tubular member and inner shaft (or tube) assembly such as by a rotation knob operatively coupled with a portion of one of the bayonet mounts so that rotation of the rotation knob causes rotation of the bayonet connector assembly and the outer tubular member and inner shaft (or tube) mounted thereto (rotating as a unit). Thus, the bayonet connector assembly can be rotationally mounted on the handle assembly such that the bayonet connector assembly can be rotated with respect to the handle assembly.

In addition, when the inner shaft is hollow (i.e., tubular) the assembly comprising the outer tubular member and inner tubular member can be mounted over another shaft. In some embodiments the fabrication of a medical device wherein an assembly comprising an outer tubular member and inner tubular member located therein can be configured as a replaceable component allowing the remainder of the device (handle assembly and optional shaft extending therefrom) to be reusable, and/or as a removable component in order to facilitate cleaning and sterilization of the device. The latter aspect is useful since tubular members, even more so concentrically arranged tube/shaft or tube-within-a-tube arrangements, are difficult to adequately clean and sterilize.

The above-described embodiments can be used for a variety of medical devices, both powered and non-powered. One particular embodiment of a medical device comprising concentrically arranged inner and outer tubular members mountable to a handle assembly using a pair of axially aligned bayonet mounts comprises an ultrasonic surgical instrument that includes a mechanism for clamping tissue against an ultrasonic end-effector (or blade). The ultrasonic surgical instrument, sometimes referred to as ultrasonic shears, can be used for tissue cutting, coagulation, and/or clamping during surgical procedures, in both open surgical procedures as well as laparoscopic or endoscopic procedures. Since the end-effector is selectively ultrasonically vibrated, the instruments described herein can also be used to grasp and manipulate tissue without ultrasonic vibration of the end-effector. When the end-effector is ultrasonically vibrated, tissue can be grasped with the instrument for tissue coagulation, as well as tissue cutting (depending on the amount of pressure applied by the clamp arm. The clamp arm is also selectively deployable, such that the end-effector can be used without clamping in order to apply ultrasonic energy to tissue.

Prior art ultrasonic surgical shears are typically designed as single-use devices, which are expensive to manufacture. These devices often have limited life due to the tissue pad wearing out and the device being extremely difficult to clean. Expense is due to the cost of components, primarily the ultrasonic components. Due to the difficulty in cleaning and sterilizing the instrument, ultrasonic surgical shears are typically not re-used with another patient, even if the tissue pad portion of the clamp arm is not worn.

Embodiments described herein provide a way to replace parts that wear out and are difficult to clean while making it easier to clean the remaining parts. Reusable parts can be priced less than a new device. By creating a way to reuse the most expensive components of the shears (the handle assembly and waveguide), costs passed on to patients and their insurers can be reduced, making the ultrasonic surgical shears available for a broad range of procedures. For example, ultrasonic shears comprise a pair of jaw members. Typically, one of those jaw members (the end-effector or blade) is fixed on the end of a waveguide, while the other jaw member (e.g., a clamp arm) is pivotally mounted adjacent the end-effector. In embodiments described herein, the movable jaw member (e.g., a clamp arm) is part of a removable and replaceable actuating assembly comprising a pair of concentrically arranged tubes having the movable jaw member movably (e.g., pivotally) mounted at the distal end of the actuating assembly. The other jaw member, which is typically fixed (i.e., non-pivoting) but may alternatively be pivotally mounted at the distal end of a waveguide, remains attached to the instrument.

The approach taken in embodiments described herein is to replace all of the distal mechanical assembly except for the blade. The clamp arm, tissue pad, inner tube and outer tube are removed, exposing the distal blade and waveguide for cleaning and sterilization. In some embodiments, this is accomplished using a double-bayonet mounting arrangement. A first bayonet mount is used to engage the outer tube with the handle assembly, while a second bayonet mount is used to engage the inner tube with the handle assembly. Each bayonet mount generally comprises a female bayonet coupling comprising one or more slots for receiving a mating protrusion, e.g., in the form of a pin (sometimes referred to as a lug), of the corresponding male bayonet coupling. Both the female and male couplings are generally provided on cylindrical structures, with the cylindrical structure on which the female coupling is located received within the interior of the cylindrical structure on which the male coupling is located. The mating pin(s) of the male bayonet coupling extend orthogonal to the common longitudinal axis. In one particular embodiment, the mating pin(s) of the male bayonet coupling extend radially inward from the interior of a cylindrical portion thereof, and each mating pin is received within a corresponding slot in a female coupling arranged on a tubular shaft. The female bayonet couplings are axially aligned such that their bayonet slots extend circumferentially about a common longitudinal axis (e.g., the longitudinal axis of a waveguide and a clamp assembly, as shown in the figures and further described herein).

In the embodiments further described herein, the male bayonet couplings are provided as part of a connector assembly retained by the handle, while the corresponding female bayonet couplings are provided on proximal portions of the tubular members of the removable assembly (e.g., the removable clamp assembly).

One embodiment described herein provides an ultrasonic surgical instrument having an arrangement for disassembling the instrument for ease of cleaning and sterilization and/or to replace one or more worn components. In particular, embodiments described herein comprise an ultrasonic surgical instrument in the form of ultrasonic shears (also known as an ultrasonic clamp coagulator) having a clamp arm adapted for clamping tissue against an ultrasonic end-effector located at the distal end of a waveguide. The clamp arm is provided as part of a clamp assembly comprising concentric tubular members, with the clamp arm pivotally mounted on the distal end of the clamp assembly for pivotal movement with respect to the end effector. The concentric tubular members are axially translatable relative to one another such that relative movement (e.g., the inner tubular member sliding within the outer tubular member, while the latter is stationary) pivotally moves the clamp arm with respect to said end-effector. The waveguide is affixed to a handle assembly, from which the waveguide extends. The clamp assembly is removably attachable to the handle assembly as a unit, by sliding the clamp assembly over the waveguide. As a result, the clamp assembly, which typically becomes worn faster than the waveguide and end-effector (particularly the clamp arm portion) and which is difficult to clean and sterilize due to the close fitting concentric tubes, can be replaced rather than having to discard the entire instrument.

In some embodiments of the present disclosure, the ultrasonic surgical instrument includes a transducer adapted to convert electrical energy into mechanical motion. In other embodiments, such a transducer is attachable to the instrument, with the ultrasonic surgical instrument including a handle assembly adapted to receive the transducer. The ultrasonic surgical instrument further comprises a waveguide adapted to be acoustically coupled to the transducer, and to transmit ultrasonic energy to an end-effector (also known as a blade) located at the distal end of the waveguide. A support tube extends from the handle assembly and surrounds at least a portion of the waveguide, terminating proximal to the end-effector. A clamp arm is pivotally mounted to the distal end of the support tube. An actuation member, configured to cause the pivotal movement of the clamp arm against the waveguide, is also provided. The actuation member is configured as a second tube coaxial with the support tube. While embodiments described herein locate the actuation member within an outer support tube, with the waveguide extending through the interior of the actuation member, in alternative embodiments the support tube is located within the actuation member. The actuation member, support tube and clamp arm comprise the clamp assembly, and are configured to be detached from the ultrasonic surgical instrument to provide for cleaning and sterilization of the ultrasonic surgical instrument.

Figure 2:
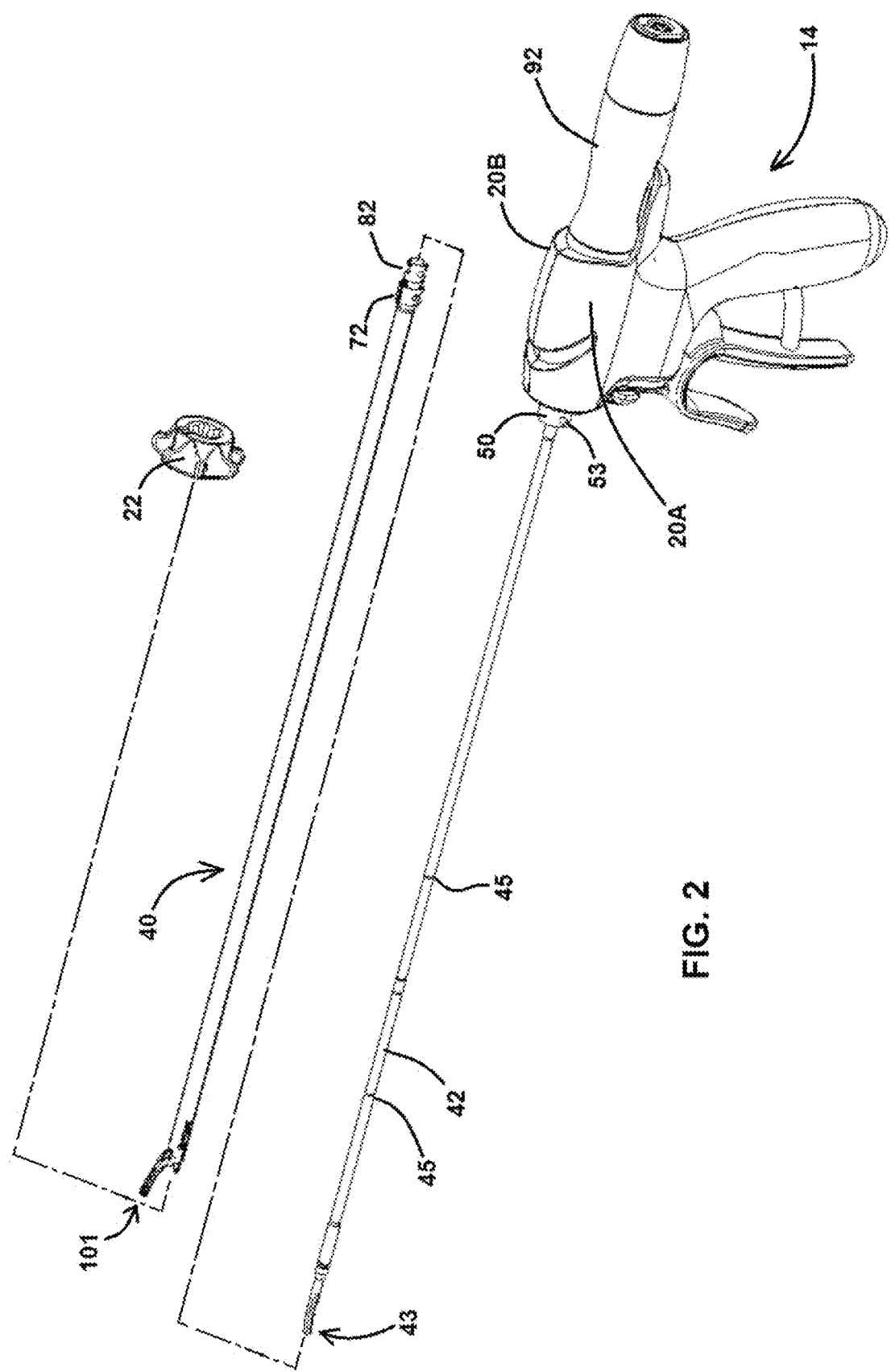
FIG. 2 is a partially disassembled view of the ultrasonic surgical instrument of the system of FIG. 1.

FIG. 1 depicts one embodiment of an ultrasonic surgical system (10), generally comprising an ultrasonic surgical instrument (12) (configured as ultrasonic surgical shears), an exemplary generator (90) and an ultrasonic transducer (92). It will be understood that generator (90) and transducer (92) are merely exemplary, as ultrasonic surgical instrument (12) can be used with any of a variety of generators and transducers. Transducer (92) includes a housing (94) which is configured to be at least partially received within the instrument handle assembly (14), as depicted in FIG. 2 and as further described herein. In the particular embodiment shown, the transducer housing (94) is also configured to facilitate grasping and manipulation of the transducer by a medical practitioner during various surgical procedures. In alternative embodiments, the transducer can be incorporated into the housing of the surgical instrument (12), in which case a separate transducer housing is not necessary. It should be noted that, in FIG. 1, the clamp arm (101) and end effector (43) are been rotated 180° from their orientation depicted in FIG. 2, using rotation knob (22) as further described herein.

The proximal end of the transducer housing (94) includes an electrical connector (e.g., a plug or a socket) for operative connection to the generator (90) via a mating connector (91) provided at the end of a cable similarly connected to the generator (90). Thus, an electrical drive signal comprising an alternating current of ultrasonic frequency is supplied from the generator (90) to the transducer (92) via the cable and connector (91). Transducer (92) converts the drive signal into a standing, ultrasonic vibrational wave in the transducer, including the distal portion (95) of the transducer horn (or velocity transformer, not shown) which protrudes from the distal end of housing (94). In the embodiment shown, the transducer housing (94) also includes a threaded projection (99) at its distal end, adjacent distal portion (95) of the transducer horn.

A threaded mounting stud (98) is secured to the distal portion (95) of the transducer horn, such as by being threadably and adhesively secured within a threaded bore (see FIG. 3) in distal portion (95). Thus, threaded stud (98) extends distally away from the distal end wall (96) of distal portion (95) of the transducer horn. It should also be pointed out that the distal end wall (96) of distal portion (95) of the transducer horn is located at an antinode of the standing vibrational wave produced by the transducer (92). By way of example, generator (90) and transducer (92) in the depicted embodiment are configured to generate a standing vibrational wave having a frequency of about 55 kHz. However, various other ultrasonic frequencies may be employed, such as between about 20 and about 120 kHz.

Figure 3:
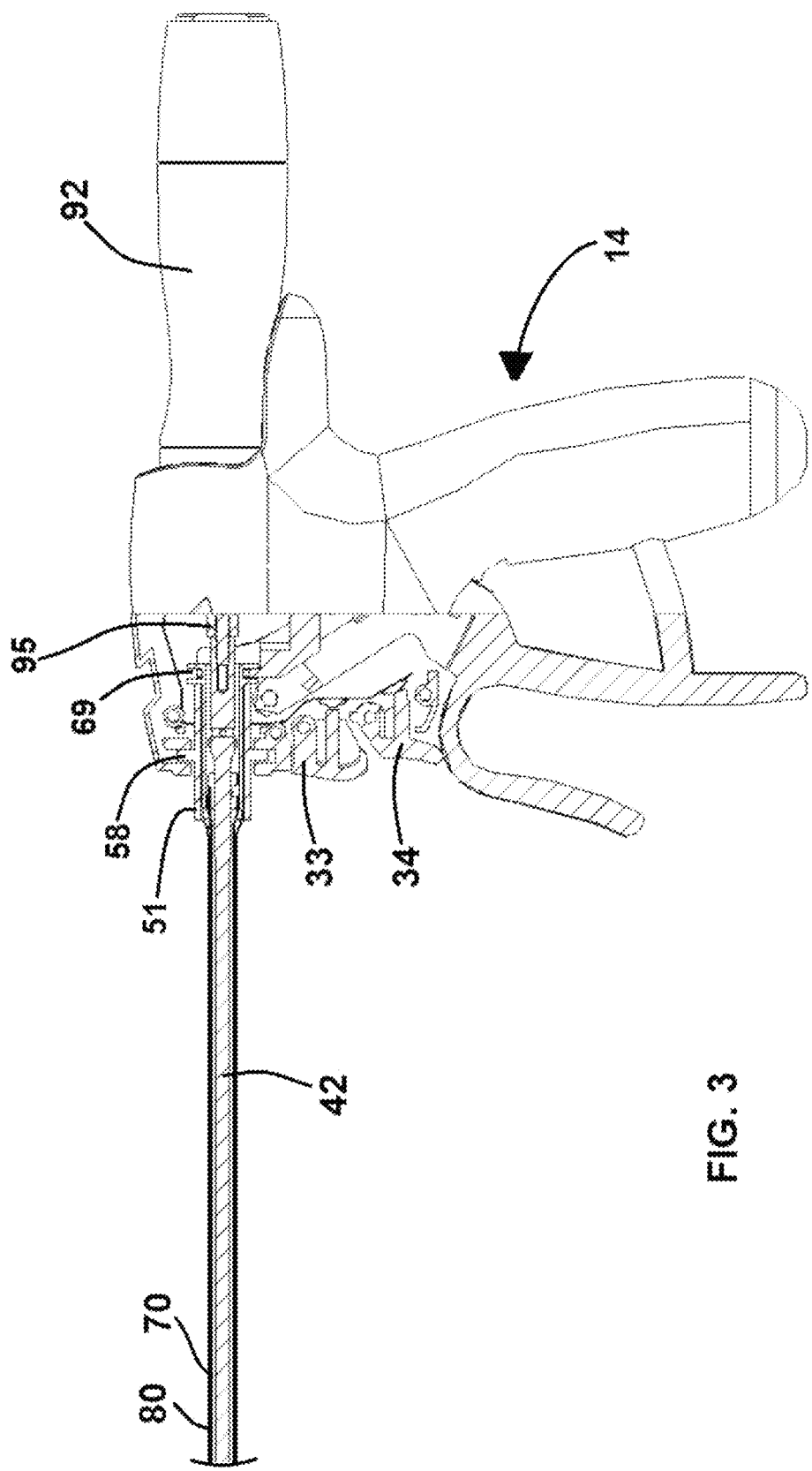
FIG. 3 is a side, partial cross-sectional view of the handle assembly with installed transducer and a portion of the clamp assembly of the ultrasonic surgical instrument of FIG. 2.

The ultrasonic surgical instrument (12) can be operatively coupled to the transducer (92) in a variety of ways. In the embodiment shown, and as best seen in FIG. 3, the proximal end of a waveguide (42) includes a threaded bore (44) that extends inwardly (i.e., distally) from the proximal end wall of the waveguide (42). The threaded bore (44) is sized and configured to threadably receive mounting stud (98) of transducer (92) therein for operatively coupling the waveguide (42) to the transducer (92). When the proximal end of the waveguide is threaded onto the mounting stud (98) of the transducer (92), the proximal end wall of the waveguide is in abutment with the distal end wall (96) of distal portion (95) of the transducer horn. When coupled in this manner, the standing vibrational wave produced in the transducer is propagated along the length of the waveguide (42) to the end effector (43) located at the distal end of the waveguide.

The ultrasonic surgical instrument (12) comprises a handle assembly (14), a clamp assembly (40) and a waveguide (42) located within the clamp assembly except for the end effector (43) protruding from the distal end of the clamp assembly. The handle assembly (14) includes a main housing (15) and a handgrip (16) extending downwardly away from the housing (15). The handle assembly (14), particularly the handgrip (16) thereof, is adapted to be held by a medical practitioner during use in order to facilitate grasping and manipulation of the instrument, while isolating the user from the ultrasonic vibrations. An actuating lever (18) is mounted to the handle assembly (14) for pivotal movement towards and away from the handgrip (16) to cause pivotal movement of the clamp arm located at the distal end of the clamp assembly (40). As an alternative to the pistol-style grip shown, the handle assembly (14) can have any of a variety of alternative configurations such as a scissors-like grip arrangement like that shown in U.S. Pat. No. 6,214,023. The main housing (15) is open at its proximal end such that the distal end of the transducer (92) can be inserted into the interior of the main housing, as depicted in FIGS. 2 and 3. Once inserted, the transducer is rotated while the handle assembly (14) is held stationary, such that the mounting stud (98) is threadably received in the threaded bore (44) in the proximal end of the waveguide (42) (as best seen in FIG. 3).

The handle assembly (14) also includes a support arm (19) that extends proximally away from the main housing (15), immediately below the opening through which the transducer is inserted into the main housing. The support arm (19) includes an arcuate upper surface such that the transducer (92) can be slid along this arcuate upper surface into the main housing, with the mounting stud (98) of the transducer aligned with the threaded bore in the proximal end of the waveguide (42). In this manner, the support arm (19) facilitates operative coupling of the transducer (92) to the waveguide (42) of the surgical instrument (12). In the embodiment shown, the interior of the main housing (15) includes support ribs against which the transducer housing will abut when the transducer is operatively coupled to the waveguide. However, the transducer (92) is rotatable within the main housing (i.e., the transducer is only secured to the waveguide). In this manner, the transducer will rotate along with the clamp assembly (40) and waveguide (42) during use, remaining in operative engagement with the waveguide (42) (as further described below).

In the depicted embodiment, the handle assembly (14) comprises first and second mating halves (20A, 20B), joined to one another along a seam in any of a variety of conventional manners known to those skilled in the art (e.g., welding, adhesives, snap-fit, etc.). It will be understood that a unitary construction can be used for handle assembly (14), or more than two mating sections joined to one another in a variety of manners. The handle assembly (14), as well as actuating lever (18), can be constructed from a suitable (i.e., sterilizable) plastic, or other sterilizable material such as various metals.

The clamp assembly (40) extends distally away from the distal end of main housing (15), and an outer support tube (70), and an inner tubular actuation member (80). The waveguide (42) is located inside the tubular actuation member (80). As further described herein, waveguide (42), outer support tube (70), and actuation member (80) are connected to one another via a male bayonet connector assembly (48) such that they can be rotated as a unit (together with the ultrasonic transducer (92)) relative to handle assembly (14), using a rotation knob (22) through which the waveguide (42) extends into the main housing of the handle assembly. The clamp assembly (40) and waveguide (42) can be rotated using the rotation knob (22) in order to present the end effector (43) and associated clamp arm (101) at the desired orientation during use. During use, rotation of the rotation knob (22) relative to the handle assembly (14) causes the rotation of the clamp assembly (40) and waveguide (42) as well as the transducer (92) operatively connected thereto relative to the handle assembly (14). In the depicted embodiment, the rotation knob (22) is also used to retain a portion of the bayonet connector assembly (48) within the handle assembly (14), and hence maintains the instrument (12) in its assembled form.

The waveguide (42) is adapted to transmit ultrasonic energy from the transducer (92) to an end-effector (43) located at the distal end of the waveguide (42), with the waveguide being flexible, semi-flexible or rigid. As is known to those skilled in the art, the waveguide (42) can include one or more changes in diameter or other features that serve to, among other things, adjust the amplitude and/or frequency of the vibrational wave propagating the length of the waveguide. By way of example, a reduction in diameter, particular when located at or near a vibrational node, will amplify the mechanical vibrations transmitted through the waveguide (42) to the end-effector (43). Various other features can be provided on the waveguide in order to control the gain (positive or negative) of the longitudinal vibration along the waveguide (42), as well as to tune the waveguide to the desired resonant frequency of the system. Thus, waveguide (42) can be have any of variety of suitable cross-sectional dimensions, including a substantially uniform cross-section, tapers at various locations along the waveguide (42) to provide two or more segments of different cross-section, or even tapered along its entire length.

The waveguide (42) can be made from any of a variety of materials, particularly various medically and surgically acceptable metals such as titanium, titanium alloy (e.g., Ti6Al4V), aluminum, aluminum alloy, or stainless steel. In some embodiments, such as that shown, the end effector (43) and waveguide (42) are formed as a single unit, such as fabricated from a single metal rod that has been milled so as to provide the desired features. Alternately, the waveguide and blade may comprise two or more separable components of the same of differing compositions, with the components coupled to one another by, for example, adhesive, welding, a threaded stud, and/or other suitable ways known to those skilled in the art. For example, the end-effector (43) can be connected to the waveguide (42) by a threaded connection, a welded joint, or other coupling mechanisms.

The waveguide (42) is configured so that, during use, the distal end of the end-effector (43) will be disposed at (or near) a vibrational anti-node of the system in order to tune the acoustic assembly to a desired resonant frequency when the end effector is not under load (i.e., not in contact with tissue). When the ultrasonic transducer (92) is energized, the distal end of the end-effector (42) will vibrate longitudinally, and optionally transversely, particularly when the end-effector is curved as shown.

The end-effector (43), sometimes referred to as a blade, can have any of a variety of shapes and configurations. For example, the end-effector can be a cylindrical rod. Alternatively, end-effector (43) can be curved, as seen in FIG. 2, with the associated claim arm (101) similarly curved.

Figure 15:
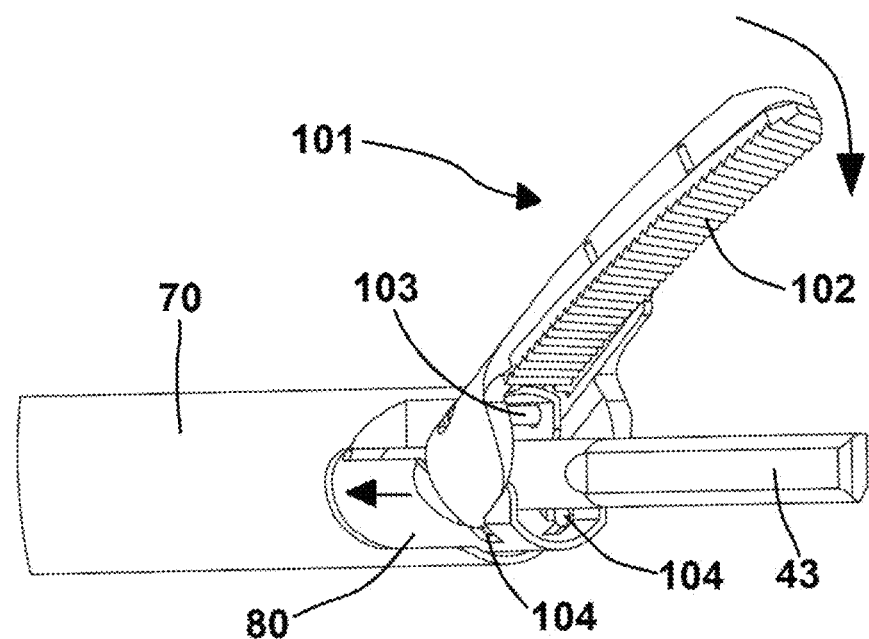
FIG. 15 depicts a side perspective view of the distal end of the clamp assembly and waveguide of the instrument of FIG. 2.

When assembled (as further described herein), the waveguide (42) is positioned within the hollow interior of tubular actuation member (80), which in turn is positioned within the hollow interior of the outer support tube (70). When assembled, at least a portion of the end-effector (43) extends beyond the distal end wall of the actuation member (80) and the distal end wall of the outer support tube (70), as seen in FIG. 15. Except for a proximal portion of the waveguide located within the handle assembly, the waveguide is located within the tubular actuation member (80), although in alternative embodiments a portion of the distal end of the waveguide can protrude beyond the distal ends of the actuation member (80) and support member (70). Of course, it will be understood that the waveguide (42), end-effector (43), actuation member (80) and/or support member (70) can be configured such that either more or less of the end-effector (43) extends beyond the distal ends of the actuation member (80) and support member (70).

Figure 4:
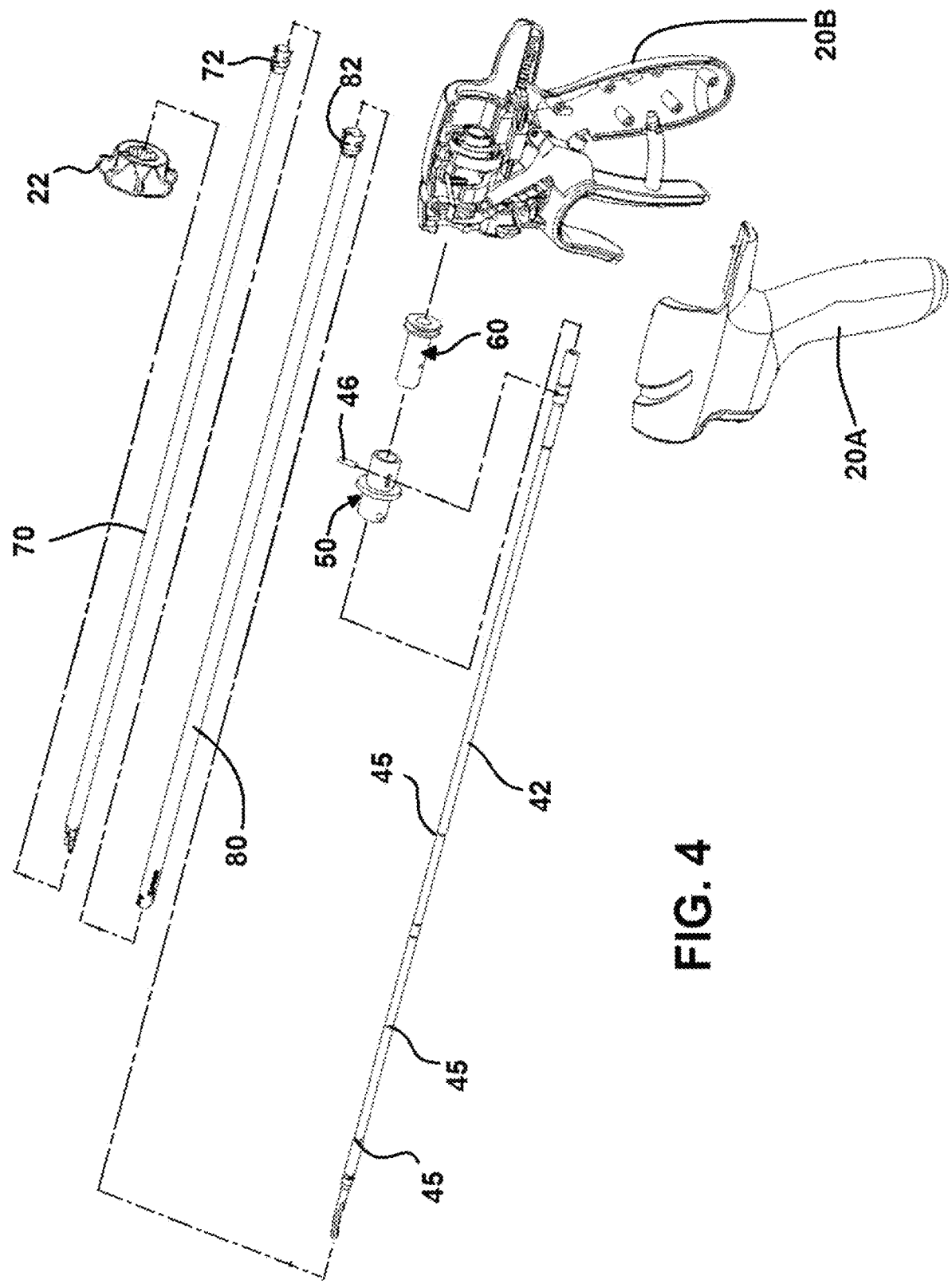
FIG. 4 is an exploded perspective view of the ultrasonic surgical instrument of FIG. 2.

During use, various forces applied at the end-effector (43) will tend to cause lateral deflection of the waveguide (42) within the tubular actuation member (80). In order to prevent contact between the inner wall of the tubular actuation member (80) and the waveguide (42), thereby limiting or preventing potential damage to the ultrasonic instrument (12) as well as damping of the standing wave, one or more spacers are provided between the waveguide (42) and the interior of tubular actuation member (80) in order to maintain the waveguide (42) in the center of the actuation member (80) (i.e., the longitudinal axis of the waveguide (42) aligned with the longitudinal axis of the actuation member (80)). In the embodiment shown in FIG. 4, resilient rings (45) are provided on the exterior of waveguide (42), and comprise, for example, silicone rings. Since the amplitude of the longitudinal vibration of the waveguide (12) at the driving frequency (e.g., 55 kHz) during use is zero at the nodes of the standing wave, the resilient rings (45) are located at or near the vibrational nodes of the waveguide (42) in order to limit damping of the standing wave. The resilient rings (45) also permit the actuation member (80) to be translated (i.e., advanced distally) over the waveguide (42) for actuation of the clamp arm (101), as explained further herein.

Referring now to FIGS. 7-13, a male bayonet connector assembly (48) is provided at the proximal end of the waveguide (42), and is used not only for securing the waveguide (42) to the handle assembly (14), but also for removably mounting the actuation member (80) and outer support tube (70) to the instrument (12). Bayonet connector assembly (48) includes a pair of bayonet coupling members (50, 60), wherein the second (or inner) coupling member (60) is received within the first (or outer) coupling member (50). Each coupling member (50, 60) includes one or more pins or protrusions for being received within in one or more slots on a proximal portion of either the actuation member (80) or the outer support tube (70).

As best shown in FIGS. 7-11, both first (or outer) coupling member (50) and second (or inner) coupling member (60) are tubular in configuration, each comprising a hollow cylindrical portion. Thus, first coupling member (50) comprises a hollow cylinder (51). Second coupling member (60) comprises a hollow cylinder (61) which is slidably received within the interior of the hollow cylinder (51) of the first coupling member (50). The coupling members (50, 60) are configured such that the second coupling member (60) is capable of limited axial movement with respect to the first coupling member (50). However, relative rotational movement of the coupling members (50, 60) is constrained (i.e., they only rotate together). In addition, while both coupling members (50, 60) are rotatably mounted within the handle assembly (14), only the second coupling member (60) is capable of axial movement within the handle assembly (14).

Figure 10:
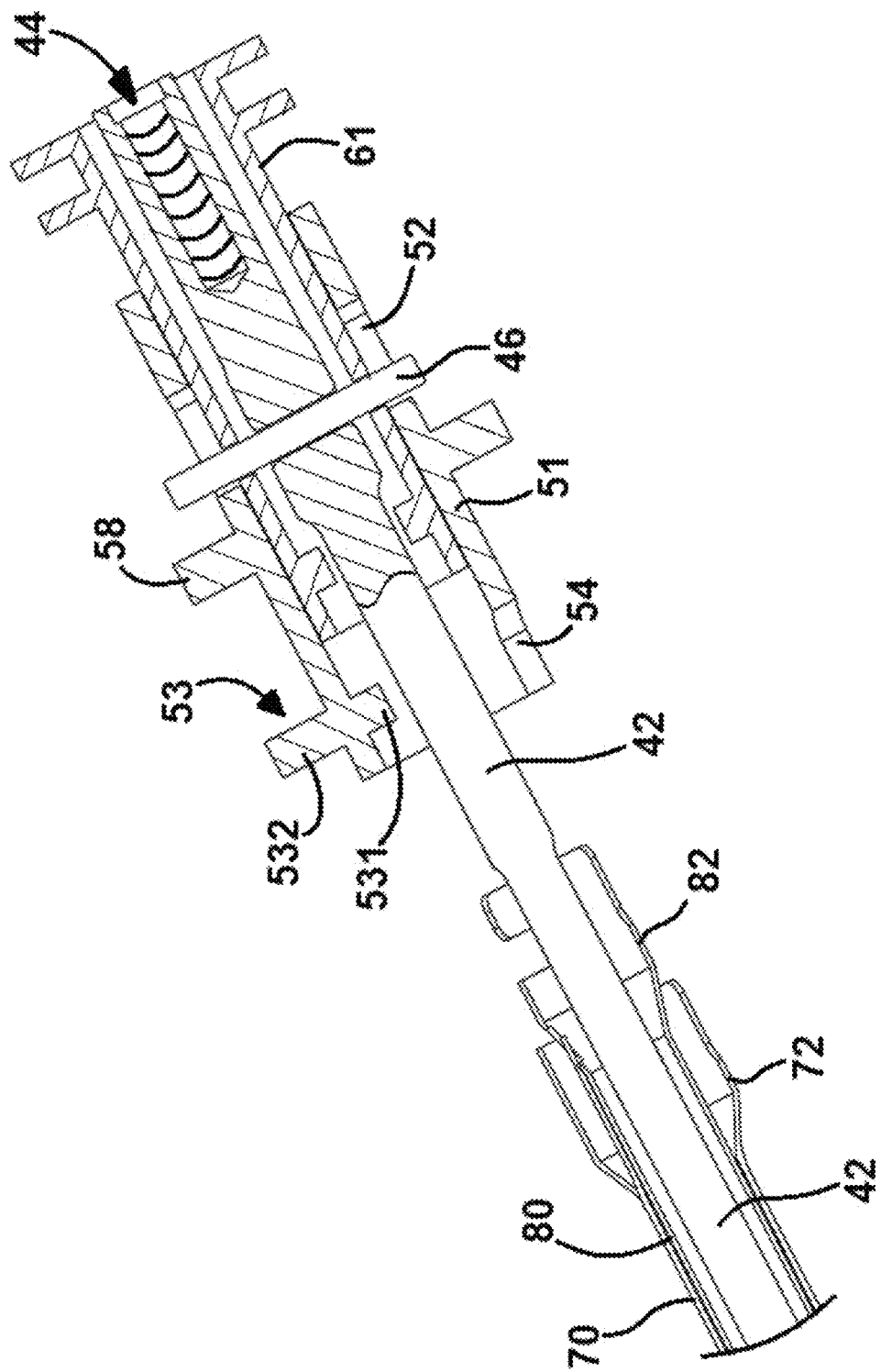
FIG. 10 is the same view as FIG. 7, shown in partial cross-section.

In particular, a pair of elongate slots (52) (e.g. oval or rectangular slots) are alignably located on opposite sides of the hollow cylinder (51) of the first coupling member (50), extending through the wall of the cylinder (51) proximal to annular flange (58) located at approximately the middle of the cylinder (51). The slots (52) extend along either side of the cylinder (51), parallel to each other and to the longitudinal axis of the cylinder. On the second coupling member (60), a pair of apertures (62) are alignably located on opposite sides of the hollow cylinder (61), extending through the wall of the cylinder (61) distal to the middle of the cylinder (61). A coupling pin (46) (see FIG. 10) extends through a bore through the waveguide (42) and through apertures (62) and slots (52), as best seen in FIG. 10. The coupling pin (46) is secured in place, such as by welding, crimping or other method known to those skilled in the art. Since the coupling pin (46) is located within the elongate slots (52) and is sized to freely slide therein, the second coupling member (60) is capable of limited axial, sliding movement within the first coupling member (50), but rotational movement of the first coupling member (50) with respect to second coupling member (60) is prevented by the elongate nature of the slots (52).

Figure 8A:
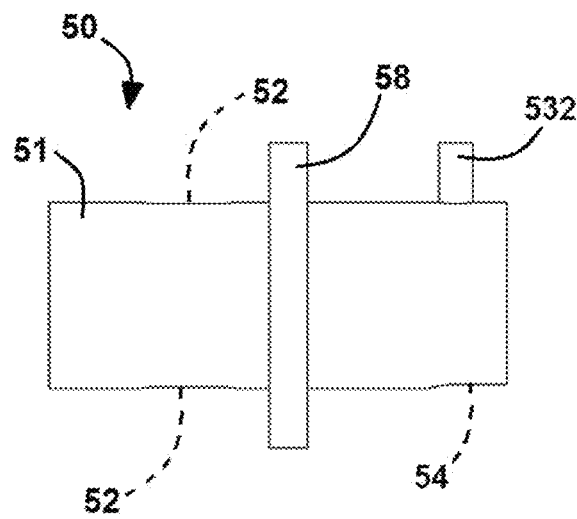
FIGS. 8A-D are top, side, perspective and front views, respectively, of the first coupling member of the male bayonet connector assembly.
Figure 8B:
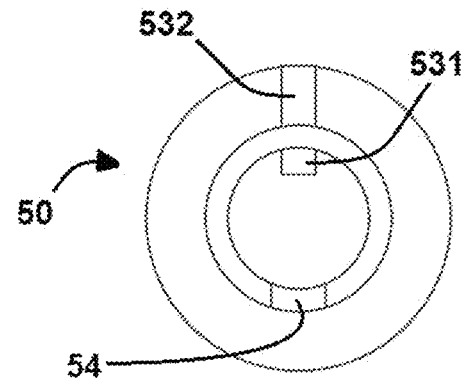
Figure 8D:
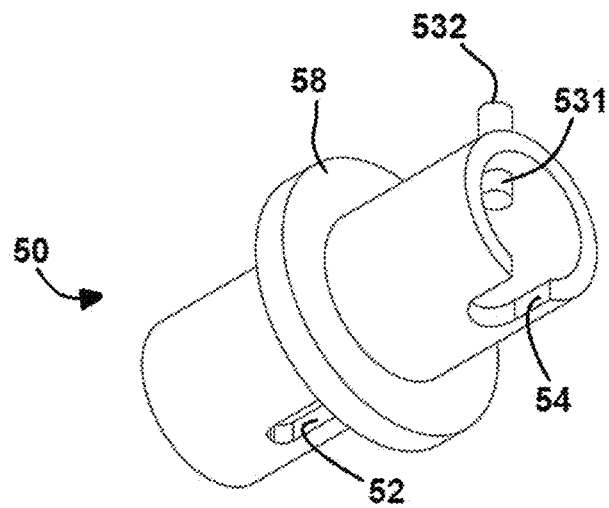
Figure 8C:
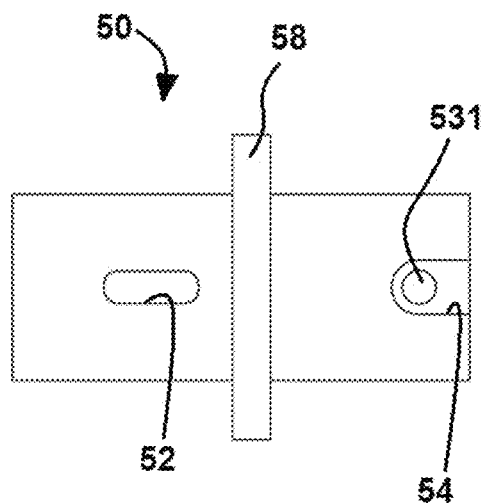

Referring now to FIGS. 8A-D, the first coupling member (50) is illustrated in top, front, side and perspective views, respectively. (FIG. 8C is essentially the same view as FIG. 8A, rotated 90°.) The first coupling member (50) further includes at least one slot (54) that is configured to receive an inward projection (26) on the rotation knob (22) for effecting rotation of the waveguide (42) and the outer support tube (70) together with the actuation member (80) to be rotated.

Figure 5:
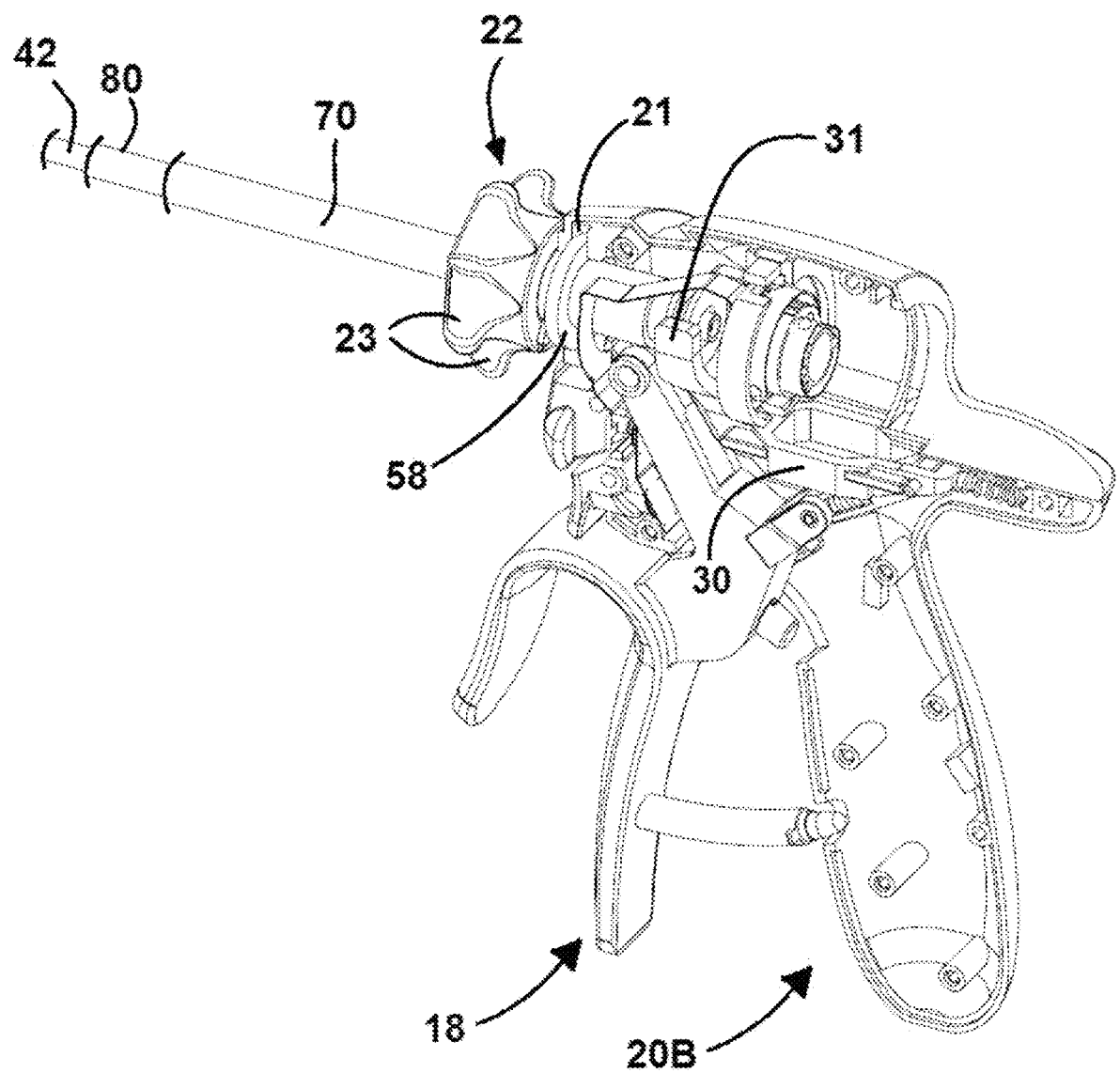
FIG. 5 is a perspective view of the handle assembly of the instrument of FIG. 2, with one half removed in order to show the interior arrangement within the handle assembly.

The first coupling member (50) has an annular retention flange (58) that extends around the circumference of the first coupling member (50) at approximately the center thereof. The annular flange (58) is rotatingly received within an annular groove (21) located within the main housing (15) of the handle assembly (14), adjacent the distal end of the main housing (15) (see FIG. 5). One half of the annular groove (21) is provided by each of the mating halves (20A, 20B) of the handle assembly (14). Thus, half of the annular groove (21) is depicted in FIG. 5. The annular flange (58) and annular groove (21) are configured such that, when the handle assembly is assembled, the annular flange (58) is captured within the annular groove (21) yet is freely rotatable within that groove. Thus, by capturing the annular flange (58) of the first coupling member (50) within the annular groove (21) within the handle assembly (14), the first coupling member (50), and hence the entire coupling assembly (48), is retained on the handle assembly while still allowing the entire coupling assembly (48) to rotate as a unit and the second coupling member (60) is capable of limited axial, sliding movement within the first coupling member (50).

A mounting pin (53) is arranged on a distal portion of the cylinder (51) of the first coupling member (50). As best seen in FIG. 10, the mounting pin (53) comprises two portions (531, 532). First mounting pin portion (531) projects inwardly into the interior of the cylinder (51) and is configured to be received within a bayonet slot (71) on the outer support tube (70). The second mounting pin portion (532) projects outwardly away from the outer surface of the cylinder (51), and is configured to be received by a pin cavity (27) in the proximal face (28) of the rotation knob (22) (as further described herein).

Referring now to FIGS. 9A-D the second coupling member (60) is illustrated in top, perspective, side and front views respectively. In addition to the hollow cylinder (61) and pair of apertures (62) located on opposite sides of the hollow cylinder (61), the second coupling member (60) further includes a pair of protrusions (64) projecting radially inwardly from opposite sides of the inner wall of the cylinder (61) thereof. Each protrusion (64) is configured for being received within one of the pair of bayonet slots (81) on the proximal end of the actuation member (80). The second coupling member (60) also includes a pair of thrust rings (68) in spaced apart relationship at the proximal end of the second coupling member (60), such that a radial slot (69) is provided between the thrust rings (68) and extends around the circumference of the second coupling member (60). As further described below, the connector assembly (48) is positioned in the handle assembly (14) such that the thrust rings (68) are positioned within a movable yoke, with one or more drive arms of the yoke extending into the radial slot (69) for axial translation of the second coupling member (60) within the first coupling member (50) while still allowing the connector assembly (48) to freely rotate, with the drive arms of the yoke traversing around the radial slot (69) as the connector assembly (48) rotates as a unit.

Figure 16A:
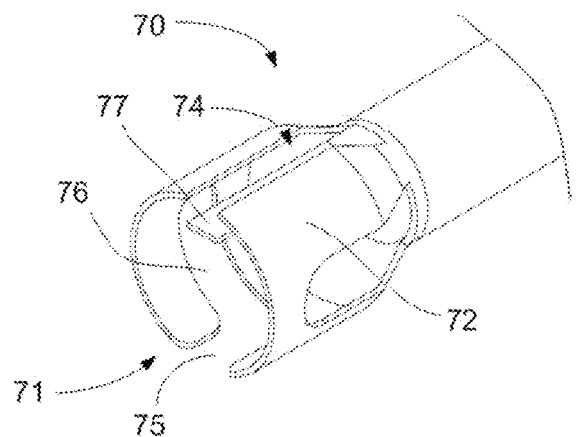
FIGS. 16A-B depict the enlarged cylindrical portion of the outer support tube.
Figure 16B:
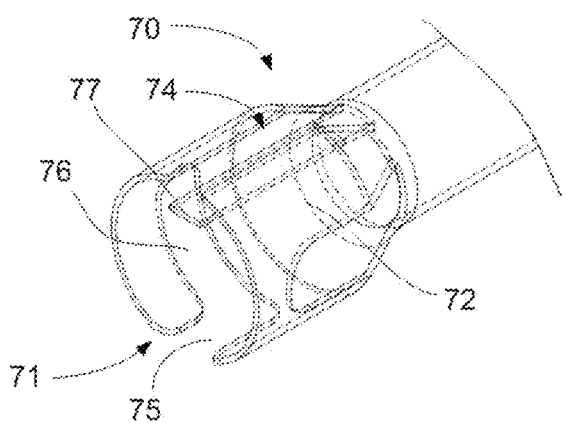

Bayonet slot (71) is located on an enlarged cylindrical portion (72) that is rigidly mounted to or formed in or on the proximal end of the outer support tube (70). Bayonet slot (71), is configured for receiving the first mounting pin portion (531) of mounting pin (53) of the first coupling member (50). As best shown in FIGS. 16A-B, the bayonet slot (71) includes an axial slot portion (75) extending from (and open to) the proximal end of the enlarged cylindrical portion (72), and a circumferential slot portion (76) extending from the axial slot portion (75) around an portion of the cylindrical portion (72). Thus, the bayonet slot (71) is L-shaped. It will be understood, however, that bayonet slot (71), as well as the bayonet slots (81) on the actuation member (80) can have a variety of an alternative shapes known to those skilled in the art, such as configuring circumferential slot portion (76) to extend helically around a portion of the cylinder (51) rather than radially as shown.

Figure 17A:
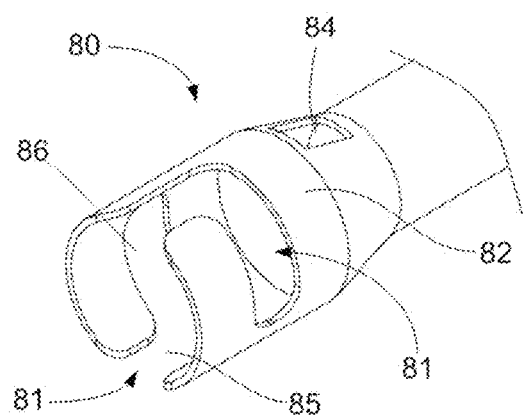
FIGS. 17A-B depict the enlarged cylindrical portion of the inner tubular actuation member.
Figure 17B:
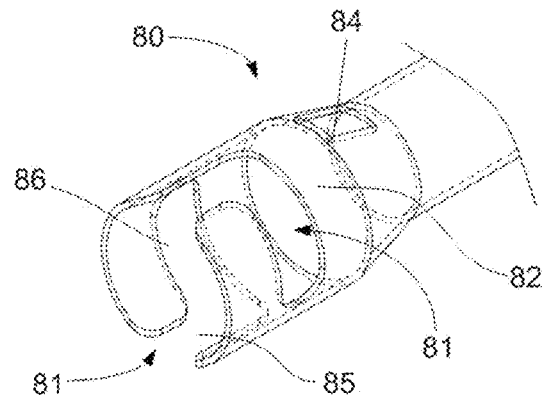

The pair of bayonet slots (81) are located on an enlarged cylindrical portion (82) that is rigidly mounted to or formed in or on the proximal end of the actuation member (80), as best seen in FIG. 17A-B, each bayonet slot (81) includes an axial slot portion (85) extending from (and open to) the proximal end of the enlarged cylindrical portion (82), and a circumferential slot portion (86) extending from the axial slot portion around a portion of the enlarged cylindrical portion (82). Thus, each bayonet slot (81) is L-shaped. In addition, the bayonet slots (81) are located on the enlarged cylindrical portion (82) 180° apart (i.e. the axial slot portions (85) are positioned directly opposite to one another). It will be understood, however, that not only may the bayonet slots (81) have a variety of an alternative shapes known to those skilled in the art, they also may be positioned at a variety of degrees of separation.

Figure 11:
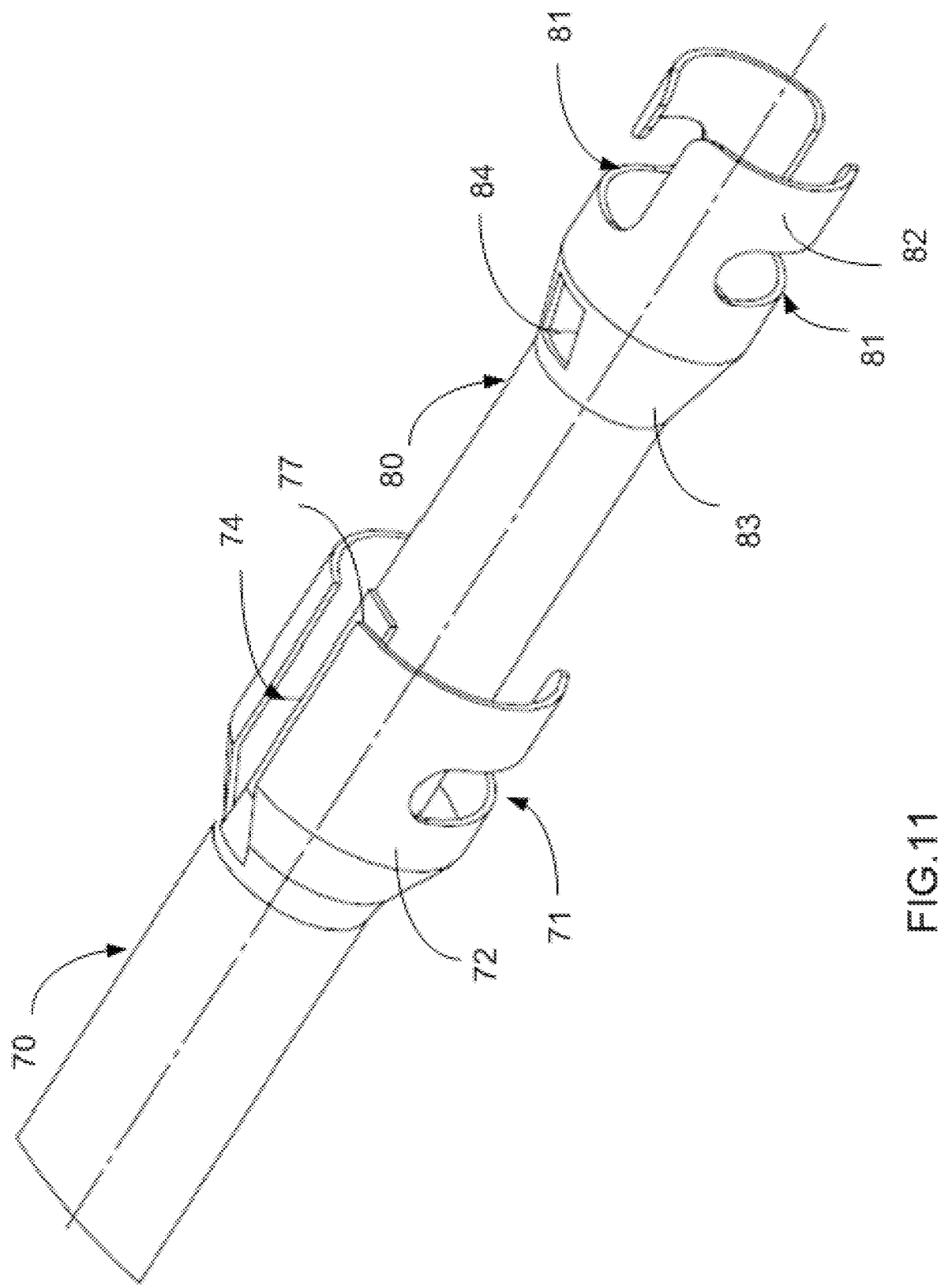
FIG. 11 schematically illustrates the engagement between the proximal portions of the outer support tube and the inner tubular actuation member of the clamp assembly.

Further, as best seen in FIG. 11, a slot (74) is provided in the proximal enlarged cylindrical portion (72) of the outer support tube (70). The slot (74) is open to the proximal end wall of the outer support tube (70). A plate (77), formed, for example, from the cutting of slot (74), is provided in the proximal portion of the outer support tube (70). Plate (77) extends proximally from the distal end of the slot (74). An opening (84) is provided in a taper portion (83) that is rigidly mounted to or formed in or on the distal end of the enlarged cylindrical portion (82) of the actuation member (80), and is configured for receiving the plate (77) of the outer support tube (70). The engagement of the plate (77) within the opening (84) constrains relative rotational movement of the outer support tube (70) and the actuation member (80) (i.e., they only rotate together), thereby also preventing the outer support tube (70) and the actuation member (80) from coming apart during assembly or disassembly.

In the embodiment shown, the outer diameter of the enlarged cylindrical portion (82) of the actuation member (80) is slightly smaller than the inner diameter of the hollow cylinder (61) of the second coupling member (60), such that the enlarged cylindrical portion (82) can be received within the hollow cylinder (61). Similarly, the outer diameter of the enlarged cylindrical portion (72) of the outer support tube (70) is slightly smaller than the inner diameter of the hollow cylinder (51) of the first coupling member (50), such that the enlarged cylindrical portion (72) can be received within the hollow cylinder (51). Furthermore, the inner diameter of the enlarged cylindrical portion (72) of the outer support tube (70) is larger than the outer diameter of the hollow cylinder (61) of the second coupling member (60), such that the enlarged cylindrical portion (72) is not capable of passing into the interior of the second coupling member (60). The enlarged cylindrical portion (72) provides a close fit within the interior of the hollow cylinder (51) in order to minimize play between the enlarged cylindrical portion (72) and the hollow cylinder (51), thereby providing a more rigid connection between the outer support tube (70) and the handle assembly (14). Similarly, the enlarged cylindrical portion (82) provides a close fit within the interior of the hollow cylinder (61) of the second coupling member (60) in order to minimize play.

When assembled, axial sliding movement of the actuation member (80) within the outer support tube (60) is permitted in order to cause the clamp arm (101) to open and close. When the coupling pin (46) is positioned at the distal ends of slots (52) (FIG. 10), the actuation member (80) is at its distal-most position and the clamp arm (101) is open (see FIG. 15). As the actuation member (80) is pulled in the proximal direction by the second coupling member (60), e.g., to the position shown in FIG. 7, the clamp member (101) pivots towards the closed position against the end effector (43) (see FIG. 15). However, since the coupling pin (46) is constrained within the elongate slots (52) even when the actuation member (80) is pulled to its furthest proximal position (i.e., clamp arm (101) is fully clamped against the end-effector (43)), actuation member (80) and outer support tube (70) can be rotated as a unit along with the waveguide (42).

It will be understood that in this embodiment the clamp assembly (40) is provided to the user in assembled form, either as a replacement for a worn clamp assembly (40) or as part of the original ultrasonic shears. To fabricate the clamp assembly (40), the distal end of the actuation member (80) is slid into the interior of the outer support tube (70), as shown schematically in FIG. 11, until the plate (77) is positioned within the opening (84). Thereafter, the clamp arm (101), which is pivotally attached to the distal end of the outer support tube (70), is attached to the distal end of the actuation member (80), as shown in FIG. 15. Thus, as actuation member (80) is pulled in the proximal direction shown in FIG. 15, the clamp arm (101) will pivot closed as also shown (by the arrow) in FIG. 15. In alternative embodiments, the clamp arm (101) is individually replaceable, rather than being part of a pre-assembled clamp assembly (40) supplied to the end user.

Figure 13A:
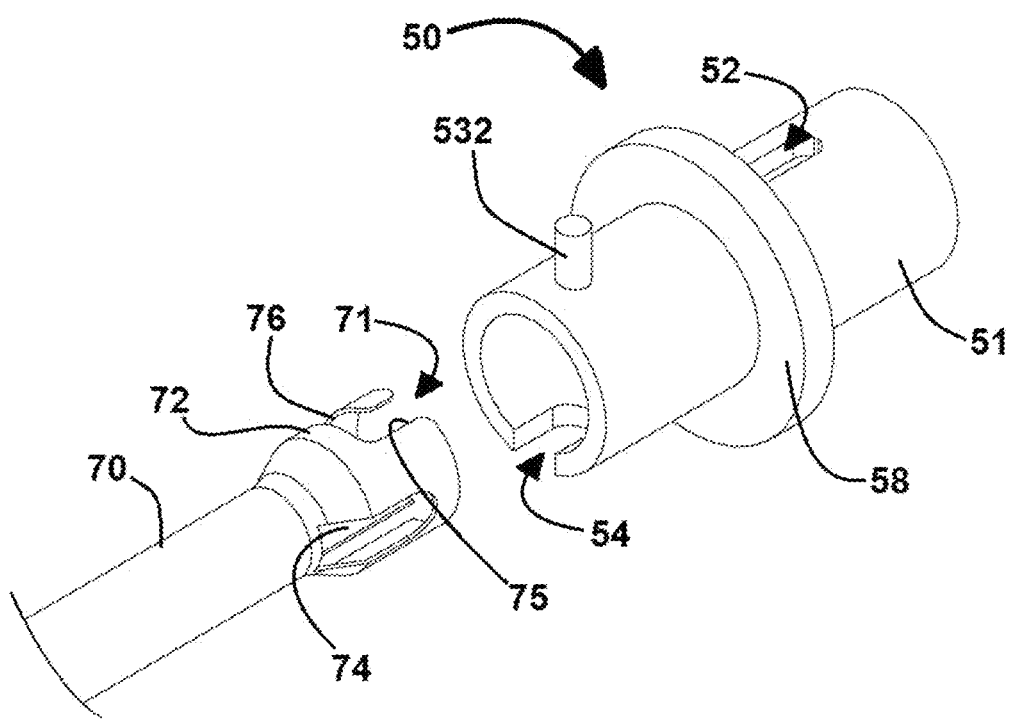
FIGS. 13A-B depict the sequence of mounting the outer support tube to the first coupling member, with the inner tubular actuation member and the second coupling member omitted for clarity.
Figure 13B:
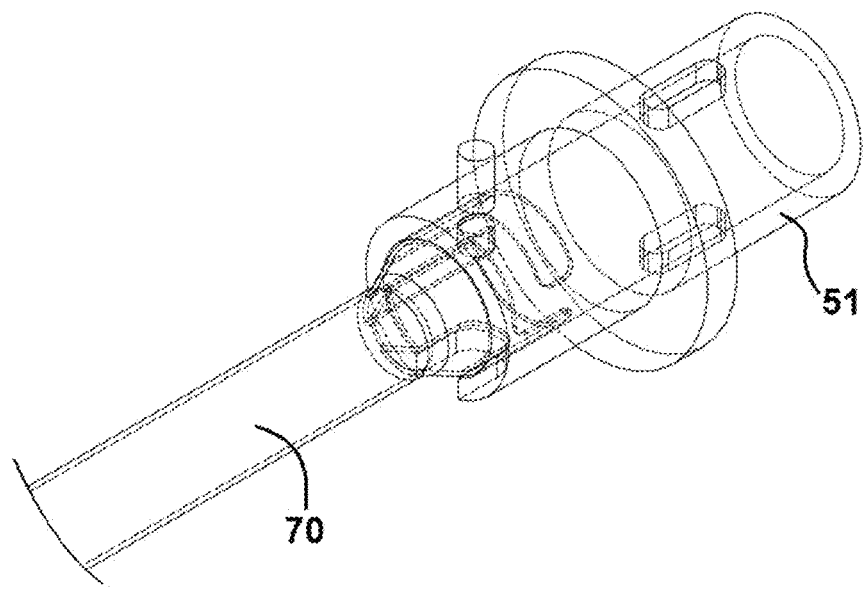

FIGS. 12A-12C and 13A-B depict the sequence of mounting the proximal end of the clamping assembly (40) to the bayonet connector assembly (48). FIGS. 12A-C best demonstrate the mounting of the actuation member (80) to the second coupling member (60), as the first coupling member (50) is omitted in FIGS. 12A-C for clarity. FIGS. 13A-B, while depicting the same sequence, best demonstrate the outer support tube (70) to the first coupling member (50). Thus, the inner tubular actuation member (80) is mounted to the second coupling member (60) substantially simultaneously with the mounting of the outer support tube (70) to the first coupling member (50). During mounting of the clamp assembly (40) to the instrument handle (14), the clamp assembly is slid over the end effector (43) and waveguide (42), as schematically depicted in FIG. 2. The clamp assembly (40) is advanced proximally down the waveguide until the protrusions (64) enters their respective axial slot portions (85) of the bayonet slots (81) of the enlarged cylindrical portion (82) of the actuation member (80), and the first mounting pin portion (531) of the mounting pin (53) enters the axial slot portion (75) of the bayonet slot (71) of the outer support tube (70). Once the protrusions (64) and the mounting pin (53) reach the proximal end of their respective axial slot portions (75, 85) the clamp assembly (40) is rotated relative to the bayonet connector assembly (48) such that the protrusions (64) and the mounting pin (53) are advanced into their respective circumferential slot portions (76, 86) until the protrusions (64) and the mounting pin (53) reach the terminus of the circumferential slot portions (76, 86). This also results in slot (74) of the outer support tube (70) being aligned with slot (54) of the first coupling member (50), as seen in FIG. 13B.

Providing relative rotation of the clamp assembly (40) with respect to the bayonet connector assembly (48) can be accomplished in a variety of ways. For example, with the transducer (92) operatively connected to the waveguide within the handle assembly (14), the user can grasp the external portion of the transducer housing with one hand, and the clamp assembly (40) (e.g., the outer support tube (70)) with their other hand and then rotate the transducer and clamp assembly relative to one another.

Alternatively, rotation knob (22) is used to apply rotational torque to the clamp assembly (40), specifically the mounting pin (53) of the first coupling member (50). Once used to mount the clamp assembly (40) to the handle assembly (14), the rotation knob (22) can then be used to rotate the clamp member (40) and waveguide (42).

Figure 14:
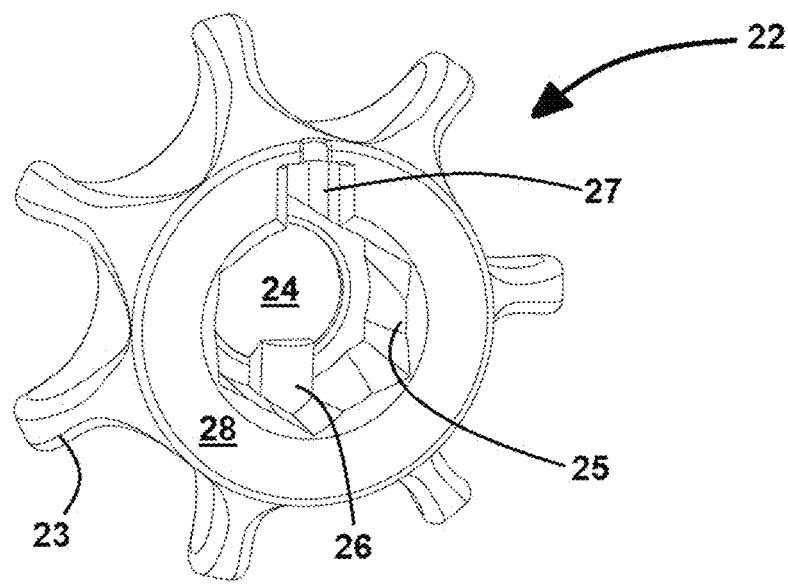
FIG. 14 is a perspective back (or proximal) view of the rotation knob of the instrument shown in FIG. 2.

Referring now to FIGS. 5 and 14, the rotation knob (22) can be used to secure the assembly of the ultrasonic surgical shears (12), allowing the double female bayonet couplings to be secured with respect to the handle assembly by an axial movement of the clamp assembly (40) followed by rotational motion of the clamp assembly, optionally using the rotation knob (22) to impart at least a portion of that rotational motion. The rotation knob (22) includes a plurality of finger supports (23) on its distal side (see FIG. 5) to facilitate applying a rotational force to the rotation knob (22). Of course, any of a variety of other structural aspects and surface features can be provided for the same purpose. A central aperture (24) is also provided in the rotation knob (22) to allow the knob (22) to be easily slid over the outside of the outer support tube (70) (see FIG. 5). A hexagonal opening (25) is provided in the proximal end surface of the rotation knob (22), as seen in FIG. 15, and is configured to engage the first coupling member (50). An inward projection

(26) extends proximally from the base of opening (25), adjacent the central aperture (24), and is received within slot (54) of the first coupling member (50) as well as slot (74) of the outer support tube. This engagement of the projection (26) within slots (54, 74) not only effects rotation of the waveguide (42) and the outer support tube (70) together with the actuation member (80), but also maintains the instrument in assembled condition during rotation as well as clamp closure.

The rotation knob (22) further includes a pin cavity (27) in the proximal face (28) of the rotation knob (22), with the pin cavity (27) extending radially outward from the hexagonal opening (25). Pin cavity (27) is sized and configured to receive the exposed portion of one of the bayonet mounting pins, particularly the exposed portion of the first coupling member mounting pin (53) (e.g. the second mounting pin portion (532) of the mounting pin (53) of the first coupling member (50)), therein. The pin cavity (27) and inward projection (26) are rotationally offset from one another by the same amount as the rotational offset between the axial slot portion (75) and the slot (74) on the outer support tube (70). Thus, the pin cavity (27) and inward projection (26) are rotationally offset from one another by 180°. When the rotation knob (22) is aligned with the clamp assembly such that the mounting pin (53) is positioned within the pin cavity (27), and the mounting pin (53) is positioned at the terminus of the circumferential slot portion (76), the inward projection (26) will be positioned within slot (74) and slot (54). In this manner, the inward projection (26) and the pin cavity (27) will prevent the outer support tube (70) as well as the actuation member (80) from rotating out of engagement with the connector assembly (48), thus maintaining the clamp assembly mounted to the handle assembly. Of course, it will be understood that the rotational offset between the pin cavity (27) and inward projection (26) can be less than or greater than 180° based on the location of the mating features on the outer support tube (70) and first coupling member (50).

After the outer support tube (70) and actuation member (80) have been coupled to the handle assembly, the rotation knob (22) is slid over the outer support tube (70) and rotated until the pin cavity (27) engages mounting pin (53) of the first coupling member (50). Rotation knob (22) is urged against the mounting pin (53) until the pin (53) is fully advanced into the pin cavity (27). The pin (53) may be held in place in pin cavity (27) using a friction fit and/or snap fit, without the need for threaded engagement of the rotation knob (22) and the handle assembly or other portion of the instrument. Alternately, rotation knob (22) may include a pin or other engagement configuration to securely but rotatably hold rotation knob (22) in place after assembly. Once the pin (53) is positioned within the pin cavity (27), the inward projection (26) will be in engagement with the slots (74, 54). The assembled bayonet connection with the rotation knob (22) prevents relative rotation of the assembled ultrasonic surgical shears while the rotation knob (22), relative rotation being undesired rotation of the outer support tube (70) and/or the actuation member (80) about the ultrasonic waveguide (42). One skilled in the art understands that there are other arrangements that could also be used, such as a friction or snap fit of the bayonet connection. However, the rotation knob (22) provides a more secure connection than the snap fit alone.

Furthermore, the rotation knob (22) can only be slid fully into place when the bayonets are properly rotationally aligned. This can be either before the knob is slid in place, or the knob (22) can be used to rotate mounting pin (53) into position. Pin cavity (27) and projection (26) are both tapered axially to allow initial misalignment (distal bayonet to proximal bayonet, and/or rotation knob (22) to bayonet assemblies) and move all components to proper alignment as the rotation knob (22) is slid into final position. Thus, the rotation knob (22) provides assistance in precisely aligning the assembly of the ultrasonic surgical shears, and giving feedback to the user that the assemblies are aligned and secure.

Since the forces on the rotation knob (22) are primarily rotational (both from a finger rotation and from the bayonet components), the rotation knob axial connection can be relatively weak, allowing it to be slid axially into place easily. In addition, first coupling member (50) and mounting pin (53) are asymmetric with respect to the longitudinal axis of the ultrasonic waveguide (42) and the outer support tube (70), permitting alignment in only one direction. This becomes more important for curved shears, where the clamp arm (101) is curved to match a curved end-effector (43), so that the direction of curvature of the end-effector matches the direction of curvature of the clamp arm.

The curved blade has to be aligned in a different direction during assembly, and then rotated into place as the bayonet connector mechanism is assembled to produce the ultrasonic surgical shears because of the curvature. By carefully choosing the rotation position of bayonet slot (71) of the outer support tube (70), users naturally line up mounting pin (53) to the bayonet slot (71) which rotationally aligns the blade for assembly.

As best seen in FIG. 15, the clamp arm (101) includes a serrated tissue pad (102), made, for example, of PTFE. As is well known to those skilled in the art, the clamp arm (101) is pivotally mounted to the distal end of the outer support tube (70) by a pivot pin (103). at the lower proximal end of the clamp arm (101), a pair of lever arms extend inwardly from the base of the clamp arm (101) into corresponding slots in the distal end of the actuation member (80). Thus, when actuation member (80) axially reciprocates within the outer support tube (60), the clamp arm (101) will pivot open and closed about the pivot pin (103). Thus, the outer support tube (70) is pivotally coupled to the clamp arm (101), which is translationally coupled to the tubular actuation member (80) to provide clamping of the clamp arm (101) against the end-effector (43), as is known in the art.

Figure 6:
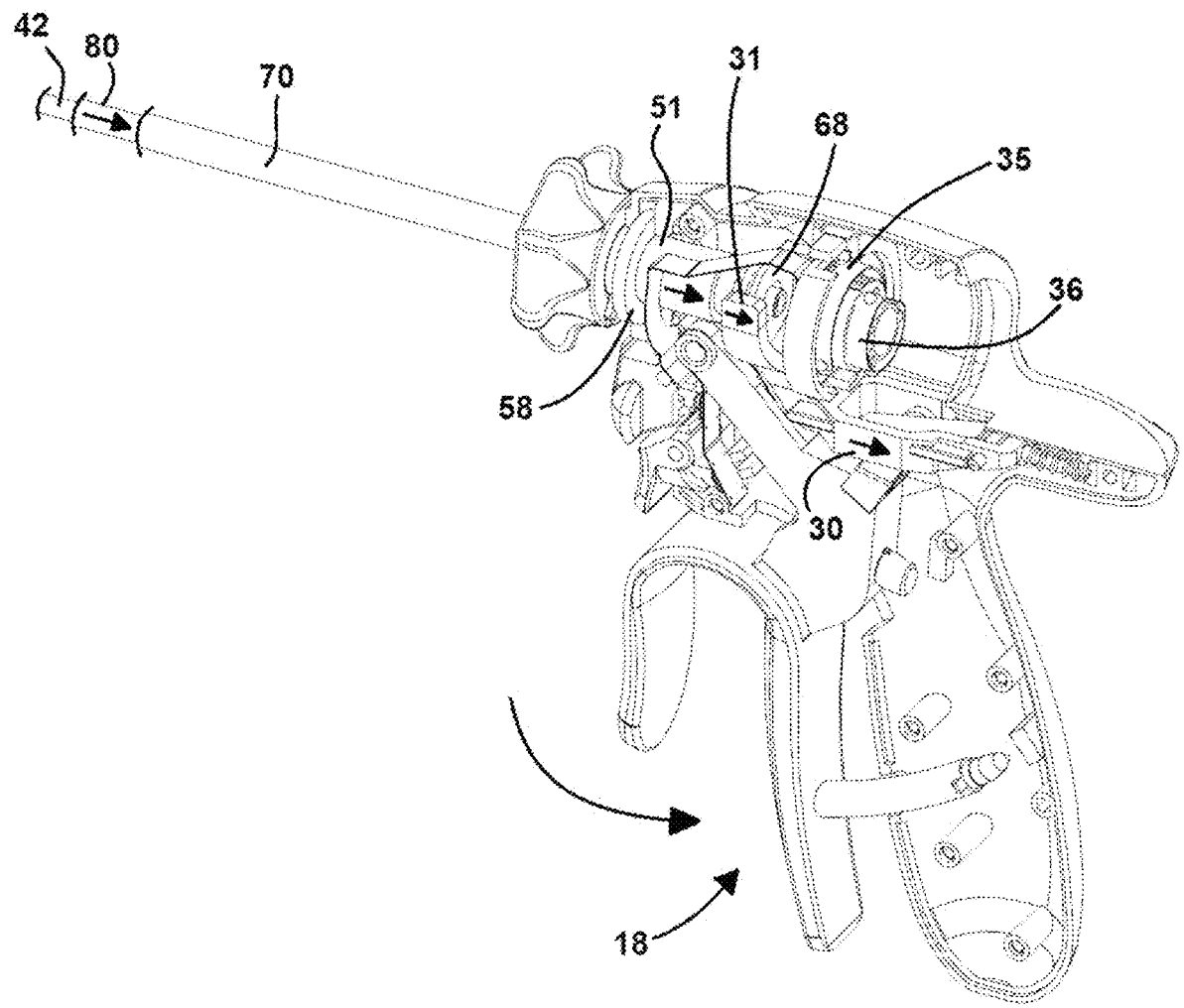
FIG. 6 is the same view as FIG. 5, with the actuating lever pulled towards the handgrip in order to urge the clamp arm against the end-effector.
Figure 7:
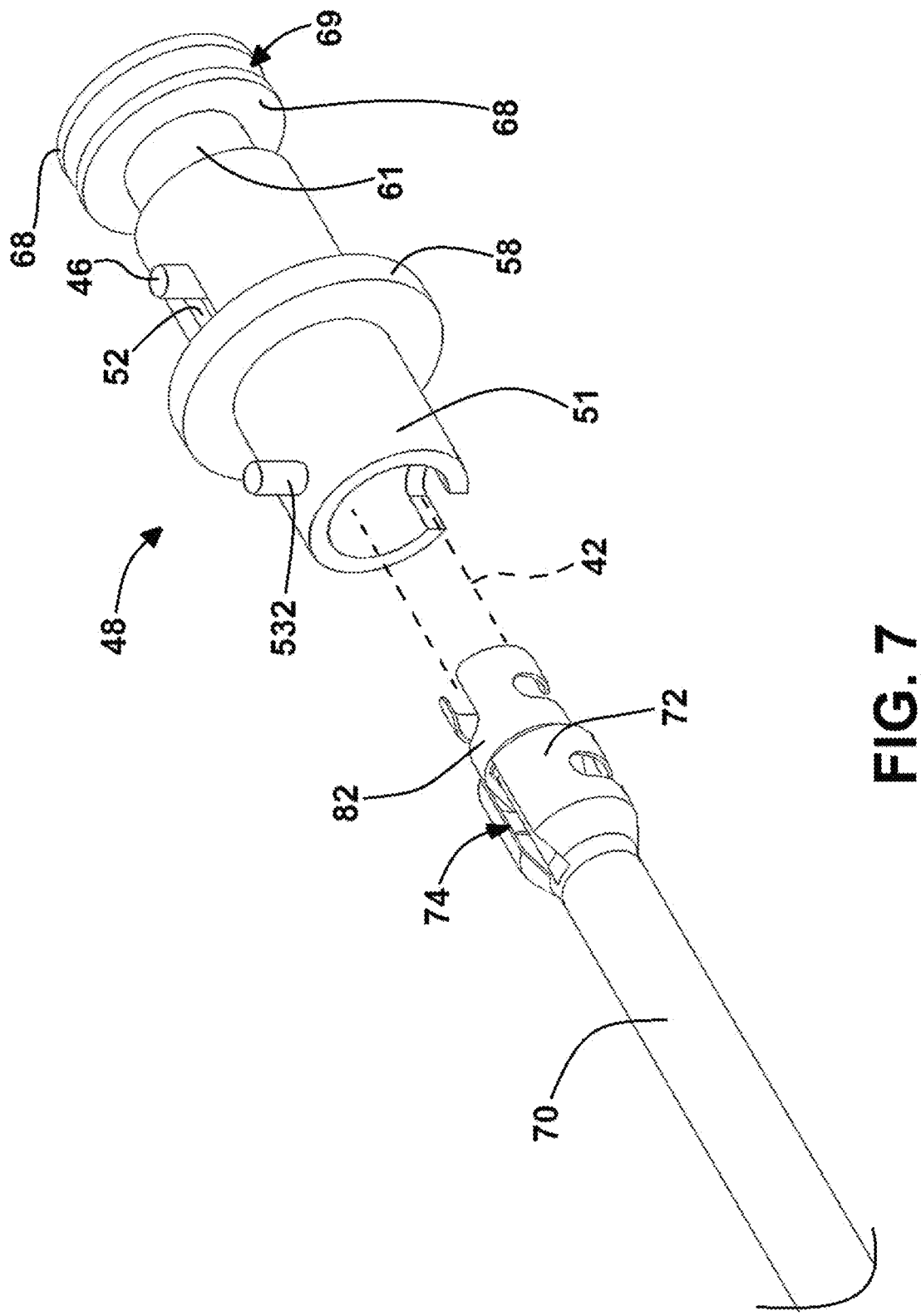
FIG. 7 schematically illustrates the dual bayonet mounting arrangement used in the instrument of FIG. 2 and its removable coupling with the clamp assembly.

Once assembled, the clamp assembly (40) can be selectively rotated with respect to the handle assembly (14) simply by rotating the rotation knob (22). In order to cause axial movement of the actuation member (80) within the outer support tube (70), actuating lever (18) of the handle assembly (14) is urged towards the handgrip (16), as shown in FIG. 6. Such pivotal movement of the actuating lever (18) causes an armature (30) to be pushed proximally, as shown in FIG. 6. The armature (30) is operatively connected to a drive yoke (31) such that the drive yoke (31) is also urged in the proximal direction, as also shown in FIG. 6. As best seen in FIG. 3, the drive yoke (31) includes a drive arm (32) that is positioned within the radial slot (69) provided between the thrust rings (68) on the proximal end of the second coupling member (60). Thus, proximal movement of the drive yoke (31) results in axial translation of the second coupling member (60) within the first coupling member (50). Since the actuation member (80) is mounted to the second coupling member (60) by the bayonet mount, this axial translation of the second coupling member (60) results in axial translation of the actuation member (80), thus clamping the clamp arm (101) against the end-effector (43).

The handle assembly (14) further includes pushbuttons (33, 34) for controlling the operation of the transducer—in particular, for controlling the delivery of energy to the transducer (e.g., on/off, power level, etc.). Such arrangements are well known to those skilled in the art, including for example, electrical slip ring conductors (35, 36) and related circuitry for providing electrical communication between the pushbuttons (33, 34) and electrical contacts on the transducer for controlling the operation of supply of power from the generator (90) to the transducer.

While various embodiments of ultrasonic shears with replaceable clamp assemblies have been described in detail above, it will be understood that the components, features and configurations, as well as the methods of manufacturing the devices and methods described herein are not limited to the specific embodiments described herein.

By way of one example, it is contemplated that the outer tube of the clamp assembly can be configured for reciprocal, axial movement with respect to the waveguide (i.e., an outer actuation member or tube) while the inner tubular member remains stationary with respect to the waveguide (yet located within the outer actuation tube). In this alternative embodiment, on the bayonet connector assembly rotatingly mounted to the handle assembly, the elongate slots for slidably receiving the coupling pin (46) of the waveguide are provided on the first (i.e., outer) coupling member so that the first coupling member is capable of limited axial, sliding movement over a portion of the second coupling member. On the second (i.e., inner) coupling member, the elongate slots are replaced by apertures such that rotational movement of the second coupling member with respect to the first coupling member is prevented, as in the previously described embodiment. In addition, in this alternative embodiment wherein the outer tube reciprocates to pivot the clamp arm, the annular retention flange is on the proximal portion of the second coupling member rather than on the first coupling member, while the spaced apart thrust rings are located on the first coupling member. Similarly, the drive yoke within the handle assembly is positioned distal to the annular groove that rotatably receives the annular retention flange of the second coupling member. In this embodiment, the drive yoke is urged distally, rather than proximally, in order to axially translate the outer tube in the distal direction, over the inner tube, thereby causing the clamp arm to be clamped against the end-effector.

Of course, any of a variety of other arrangements can be provided in order to effect axial translation of one of the tubular members of the clamp assembly with respect to the other tubular member of the clamp assembly, using axial sliding movement of one bayonet coupling within a second bayonet coupling.

As yet another alternative, the bayonet couplings can be located mid-shaft rather than at the distal end of the handle assembly (and proximal end of the clamp assembly). In this alternative, the bayonet connections would be distal to the handle assembly, but proximal to the end-effector (e.g., at approximately the mid-point of the clamp assembly, or at a location distal to the handle assembly by a distance between 30% and 70% of the length of the clamp assembly). Thus, both the support tube and actuation member would extend from the handle assembly and surround at least a portion of the waveguide, with both the support tube and the actuation member separable into two portions via a pair of concentric (i.e., axially aligned) bayonet mounts.

What is claimed is:

1. An ultrasonic surgical instrument comprising:
(a) a handle assembly;
(b) a waveguide extending distally from said handle assembly, wherein said waveguide is adapted to be acoustically coupled to an ultrasonic transducer and transmit ultrasonic energy therethrough;
(c) an end-effector located at a distal end of said waveguide; and
(d) a clamp assembly removably mounted to said handle assembly, said clamp assembly including a clamp arm pivotally mounted on the distal end of the clamp assembly for pivotal movement with respect to the end effector;
wherein said clamp assembly is removably mounted to the handle assembly by axially aligned first and second bayonet mounts, each of said bayonet mounts comprising a female bayonet coupling having at least one bayonet slot configured to matingly receive a bayonet mounting pin of a male bayonet coupling, wherein said bayonet slots are provided on said clamp assembly and extend circumferentially about a common longitudinal axis corresponding to the longitudinal axis of said waveguide.

2. The ultrasonic surgical instrument of claim 1, wherein said clamp assembly comprises a pair of tubular members concentrically arranged about the waveguide, wherein said tubular members comprise a support tube and a tubular actuation member.

3. The ultrasonic surgical instrument of claim 2, wherein said support tube and said tubular actuation member are axially translatable relative to one another such that relative movement between the support tube and the tubular actuation member causes pivotal movement of the clamp arm with respect to said end-effector.

4. The ultrasonic surgical instrument of claim 3, wherein said actuation member is located at least partially within said support tube and is axially translatable within said support tube such that axial translation of the actuation member within the support tube causes pivotal movement of the clamp arm with respect to said end-effector.

5. The ultrasonic surgical instrument of claim 4, wherein said bayonet connector assembly comprises a first coupling member and a second coupling member, wherein a portion of the second coupling member is slidably received within a portion of the first coupling member.

6. The ultrasonic surgical instrument of claim 5, wherein said first and second coupling members are rotatably mounted within said handle assembly.

7. The ultrasonic surgical instrument of claim 5, wherein said first coupling member is axially fixed with respect to said handle assembly.

8. The ultrasonic surgical instrument of claim 5, further comprising an actuating lever pivotally mounted to the handle assembly, and further wherein pivotal movement of the actuating lever causes axial movement of the second coupling member within said first coupling member, thereby causing pivotal movement of the clamp arm.

9. The ultrasonic surgical instrument of claim 2, wherein said at least one bayonet slot of the first female bayonet coupling is provided on said support tube, and said at least one bayonet slot of the second female bayonet coupling is provided on said tubular actuation member.

10. The ultrasonic surgical instrument of claim 9, wherein each of said support tube and said actuation member have enlarged cylindrical portions at their proximal ends, the cylindrical portion at the proximal end of the support tube having a larger diameter than the cylindrical portion at the proximal end of the actuation member.

11. The ultrasonic surgical instrument of claim 10, wherein said at least one bayonet slot of the first female bayonet coupling is provided on the enlarged cylindrical portion of the support tube, and said at least one bayonet slot of the second female bayonet coupling is provided on the enlarged cylindrical portion of the actuation member.

12. The ultrasonic surgical instrument of claim 9, wherein each of said at least one bayonet slots includes:
an axial slot portion extending from and open to the proximal end of the tubular member on which said at least one bayonet slot is provided; and
a circumferential slot portion extending from the axial slot portion around a portion of the tubular member on which said at least one bayonet slot is provided.

13. A method of removing the clamp assembly of the ultrasonic surgical instrument of claim 12, comprising the steps of: rotating the bayonet mounting pins out of the circumferential slot portion of its respective bayonet slot by effecting relative axial rotation of the clamp assembly with respect to the handle assembly; and thereafter axially removing each of the bayonet mounting pins from the axial slot portion of its respective bayonet slot by effecting axial, proximal movement of the waveguide out of the tubular actuation member.

14. The ultrasonic surgical instrument of claim 1, further comprising a bayonet connector assembly rotatably mounted to said handle assembly, wherein said first and second male bayonet couplings are provided on said bayonet connector assembly.

15. The ultrasonic surgical instrument of claim 14, wherein each of said first and second male bayonet couplings comprises at least one mounting pin extending orthogonal to said common longitudinal axis.

16. The ultrasonic surgical instrument of claim 15, wherein said bayonet connector assembly comprises a first coupling member and a second coupling member, wherein the second coupling member is slidably received within a portion of the first coupling member.

17. The ultrasonic surgical instrument of claim 14, wherein each of said first and second male bayonet couplings comprises at least one mounting pin extending radially inward from an interior wall of said bayonet connector assembly, and the portions of the clamp assembly having said bayonet slots are received within said bayonet connector assembly.

18. The ultrasonic surgical instrument of claim 1, further comprising a rotation knob rotatably mounted on the instrument such that the rotation knob maintains the clamp assembly mounted to the handle assembly, and such that rotation of the rotation knob causes the clamp assembly and the waveguide to rotate as a unit.

19. The ultrasonic surgical instrument of claim 18, wherein said rotation knob further comprises a pin cavity in a proximal face of the rotation knob, and said rotation knob is mounted on the instrument by urging one of said bayonet mounting pins into said pin cavity.

20. An ultrasonic surgical shears instrument comprising:
(a) a handle assembly;
(b) an ultrasonic waveguide extending distally from said handle assembly and having an end-effector at the distal end of the waveguide;
(c) a clamp assembly having a proximal end and a distal end, said clamp assembly removably and rotatably mounted to said handle assembly, said clamp assembly including
an outer support tube having a proximal end and a distal end, with at least one bayonet slot adjacent the proximal end of the outer support tube, and wherein at least a portion of said end-effector extends distally of said distal end of said outer support tube,
an inner tubular actuating member having a proximal end and a distal end, with at least one bayonet slot adjacent the proximal end of the actuating member, said actuating member positioned within said outer support tube and said waveguide positioned within said inner tubular actuating member, and
a clamp arm pivotally mounted on the distal end of said outer support tube for pivotal movement with respect to said end-effector for clamping tissue between said clamp arm and said end-effector, said clamp arm being operatively connected to said actuating member so that relative, reciprocal movement between the outer support tube and the actuating member pivotally moves said clamp arm with respect to said end-effector; and
(d) a bayonet connector assembly rotatably mounted to said handle assembly, said bayonet connector assembly comprising first and second coupling members, wherein a portion of the second coupling member is slidably received within said first coupling member, each of said first and second coupling members having at least one mounting pin configured to be matingly received in one of said bayonet slots of said outer support tube and said inner tubular actuating member for removably mounting the clamp assembly to said handle assembly.

* * * * *